(12) United States Patent
Sherwood et al.

(10) Patent No.: US 11,172,846 B2
(45) Date of Patent: Nov. 16, 2021

(54) GAS SAMPLING DEVICE

(71) Applicant: Boston Scientific Scimed, Inc., Maple Grove, MN (US)

(72) Inventors: Gregory J. Sherwood, North Oaks, MN (US); Nathaniel Stark, Plymouth, MN (US); Justin Theodore Nelson, St. Louis Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 9 days.

(21) Appl. No.: 15/787,985

(22) Filed: Oct. 19, 2017

(65) Prior Publication Data

US 2018/0110444 A1  Apr. 26, 2018

Related U.S. Application Data

(60) Provisional application No. 62/411,383, filed on Oct. 21, 2016.

(51) Int. Cl.
*A61B 5/00* (2006.01)
*A61B 5/097* (2006.01)
(Continued)

(52) U.S. Cl.
CPC ............ *A61B 5/097* (2013.01); *A61B 5/01* (2013.01); *A61B 5/0205* (2013.01); *A61B 5/08* (2013.01);
(Continued)

(58) Field of Classification Search
CPC ......... A61B 5/0816; A61B 5/742; A61B 5/01; A61B 5/097; A61B 5/087; A61B 5/082;
(Continued)

(56) References Cited

U.S. PATENT DOCUMENTS 3,661,528 A * 5/1972 Falk ................. A61B 5/097
                                              73/863.01
3,952,730 A    4/1976 Key
                       (Continued)

FOREIGN PATENT DOCUMENTS

CN    102941042     2/2013
CN    103332678    10/2013
                  (Continued)

OTHER PUBLICATIONS

Arasaradnam, R. P. et al., "Review Article: Next Generation Diagnostic Modalities in Gastroenterology—Gas Phase Volatile compund biomarker detection," Alimentary Pharmacology and Therapeutics 2014; 39: 780-789 (10 pages).

(Continued)

*Primary Examiner* — May A Abouelela
(74) *Attorney, Agent, or Firm* — Pauly, DeVries Smith & Deffner LLC

(57) ABSTRACT

The technology disclosed herein relates to, in part, a gas sampling device. According to some aspects, the gas sampling device has a housing defining an airflow aperture, a gas testing chamber and an airflow pathway extending from the airflow aperture to the gas testing chamber. The housing also defines a sensor receptacle configured to removably hold a disposable sensor test strip within the gas testing chamber and a docking structure configured to be received by a docking station.

9 Claims, 15 Drawing Sheets

(51) Int. Cl.
  *A61B 5/08* (2006.01)
  *A61B 5/01* (2006.01)
  *A61B 5/0205* (2006.01)
  *G01N 33/497* (2006.01)
  *G01N 33/543* (2006.01)
  *A61B 5/024* (2006.01)

(52) U.S. Cl.
  CPC ......... *G01N 33/497* (2013.01); *G01N 33/543* (2013.01); *A61B 5/024* (2013.01); *G01N 2033/4975* (2013.01)

(58) Field of Classification Search
  CPC ......... A61B 5/08; A61B 5/0205; A61B 5/024; A61M 16/024; A61M 16/0051; A61M 2016/0036; A61M 2202/0208; A61M 2205/3368; A61M 2230/06; A61M 2230/432; A61M 2230/50; G01N 33/497; G01N 2033/4975; G01N 21/3504; G01N 2800/12; G01N 2800/347; G01N 33/4972; G01N 33/98; G01N 2030/025; G01N 21/0332; G01N 33/543
  USPC ......... 600/300, 309, 529, 532, 538; 606/234
  See application file for complete search history.

(56) References Cited

U.S. PATENT DOCUMENTS

| | | | |
|---|---|---|---|
| 3,981,297 A | 9/1976 | Dunn et al. | |
| 4,820,011 A | 4/1989 | Umegaki et al. | |
| 4,901,727 A | 2/1990 | Goodwin | |
| 5,174,290 A | 12/1992 | Fiddian-Green | |
| 5,186,172 A | 2/1993 | Fiddian-Green | |
| 5,357,971 A | 10/1994 | Sheehan et al. | |
| 5,423,320 A | 6/1995 | Salzman et al. | |
| 5,704,368 A | 1/1998 | Asano et al. | |
| 5,834,626 A | 11/1998 | De Castro et al. | |
| 5,928,155 A | 7/1999 | Eggers et al. | |
| 6,006,121 A | 12/1999 | Vantrappen et al. | |
| 6,029,076 A | 2/2000 | Fiddian-Greene et al. | |
| 6,085,576 A | 7/2000 | Sunshine et al. | |
| 6,149,624 A | 11/2000 | Mcshane | |
| 6,192,168 B1 | 2/2001 | Feldstein et al. | |
| 6,238,339 B1 | 5/2001 | Fiddian-Greene et al. | |
| 6,248,078 B1 | 6/2001 | Risby et al. | |
| 6,312,390 B1 | 11/2001 | Phillips et al. | |
| 6,480,734 B1 | 11/2002 | Zhang et al. | |
| 6,599,253 B1 | 7/2003 | Baum et al. | |
| 6,615,066 B2 | 9/2003 | Huyberechts et al. | |
| 6,712,770 B2 | 3/2004 | Lin et al. | |
| 6,726,637 B2 | 4/2004 | Phillips et al. | |
| 6,733,464 B2 | 5/2004 | Olbrich et al. | |
| 6,781,690 B2 | 8/2004 | Armstrong et al. | |
| 6,955,652 B1 | 10/2005 | Baum et al. | |
| 6,978,182 B2 | 12/2005 | Mazar et al. | |
| 7,032,431 B2 | 4/2006 | Baum et al. | |
| 7,123,359 B2 | 10/2006 | Armstrong et al. | |
| 7,177,686 B1 | 2/2007 | Turcott et al. | |
| 7,426,848 B1 | 9/2008 | Li et al. | |
| 7,459,312 B2 | 12/2008 | Chen et al. | |
| 7,704,214 B2 | 4/2010 | Meixner et al. | |
| 7,809,441 B2 | 10/2010 | Kane et al. | |
| 7,871,572 B2 | 1/2011 | Yang et al. | |
| 7,972,277 B2 | 7/2011 | Oki et al. | |
| 7,988,917 B2 | 8/2011 | Roesicke et al. | |
| 7,992,422 B2 | 8/2011 | Leddy et al. | |
| 8,043,860 B2 | 10/2011 | Leznoff et al. | |
| 8,052,933 B2* | 11/2011 | Schirmer | G01N 1/22 422/500 |
| 8,080,206 B2 | 12/2011 | Leddy et al. | |
| 8,124,419 B2 | 2/2012 | Grigorian et al. | |
| 8,153,439 B2 | 4/2012 | Zamborini et al. | |
| 8,154,093 B2 | 4/2012 | Passmore et al. | |
| 8,157,730 B2 | 4/2012 | Tucker et al. | |
| 8,222,041 B2 | 7/2012 | Pearton et al. | |
| 8,244,355 B2 | 8/2012 | Bennett et al. | |
| 8,366,630 B2 | 2/2013 | Haick et al. | |
| 8,479,731 B2* | 7/2013 | Heinonen | A61B 5/0836 128/200.15 |
| 8,481,324 B2 | 7/2013 | Nakhoul et al. | |
| 8,494,606 B2 | 7/2013 | Debreczeny et al. | |
| 8,529,459 B2 | 9/2013 | Stahl, Jr. et al. | |
| 8,597,953 B2 | 12/2013 | Haick et al. | |
| 8,747,325 B2 | 6/2014 | Bacal et al. | |
| 8,828,713 B2 | 9/2014 | Ren et al. | |
| 8,835,984 B2 | 9/2014 | Ren et al. | |
| 8,848,189 B2 | 9/2014 | Goldshtein et al. | |
| 8,955,367 B2 | 2/2015 | Gouma et al. | |
| 9,011,779 B1 | 4/2015 | Jensen et al. | |
| 9,029,168 B2 | 5/2015 | Mannoor et al. | |
| 9,103,775 B2 | 8/2015 | Bradley et al. | |
| 9,147,398 B2 | 9/2015 | White et al. | |
| 9,147,851 B1 | 9/2015 | Bartsch et al. | |
| 9,299,238 B1* | 3/2016 | Ahmad | A61B 5/4833 |
| 9,315,848 B2 | 4/2016 | Haick et al. | |
| 9,316,637 B2 | 4/2016 | Ren et al. | |
| 9,324,825 B2 | 4/2016 | Ravesi et al. | |
| 9,366,664 B2 | 6/2016 | Jensen et al. | |
| 9,513,244 B2 | 12/2016 | Koester | |
| 9,528,979 B2 | 12/2016 | Haick et al. | |
| 9,618,476 B2 | 4/2017 | Goldsmith | |
| 9,642,577 B1 | 5/2017 | Li et al. | |
| 9,696,311 B2 | 7/2017 | Haick et al. | |
| 9,763,600 B2 | 9/2017 | Van Kesteren et al. | |
| 9,765,395 B2 | 9/2017 | Goldsmith | |
| 9,936,897 B2* | 4/2018 | Carlson | A61B 5/083 |
| 9,977,011 B2 | 5/2018 | Beck et al. | |
| 10,034,621 B2* | 7/2018 | Wondka | A61B 5/0816 |
| 10,046,323 B2 | 8/2018 | Bos | |
| 10,307,080 B2 | 6/2019 | Ssenyange et al. | |
| 10,770,182 B2 | 9/2020 | Sherwood et al. | |
| 10,852,264 B2 | 12/2020 | Kelly et al. | |
| 2002/0123749 A1 | 9/2002 | Jain et al. | |
| 2002/0142477 A1 | 10/2002 | Lewis et al. | |
| 2003/0051733 A1 | 3/2003 | Kotmel et al. | |
| 2004/0039295 A1* | 2/2004 | Olbrich | A61B 5/0205 600/538 |
| 2006/0130557 A1 | 6/2006 | Leddy et al. | |
| 2006/0263255 A1 | 11/2006 | Han et al. | |
| 2006/0270940 A1 | 11/2006 | Tsukashima et al. | |
| 2007/0048181 A1 | 3/2007 | Chang et al. | |
| 2007/0083094 A1 | 4/2007 | Colburn et al. | |
| 2007/0167853 A1 | 7/2007 | Melker et al. | |
| 2007/0229818 A1 | 10/2007 | Duan et al. | |
| 2007/0265509 A1 | 11/2007 | Burch et al. | |
| 2008/0021339 A1 | 1/2008 | Gabriel et al. | |
| 2008/0038154 A1* | 2/2008 | Longbottom | A61B 5/083 422/84 |
| 2008/0146890 A1 | 6/2008 | Leboeuf et al. | |
| 2008/0161709 A1* | 7/2008 | Bradley | A61B 5/0833 600/532 |
| 2008/0183910 A1 | 7/2008 | Natoli et al. | |
| 2008/0228098 A1* | 9/2008 | Popov | A61B 5/01 600/537 |
| 2008/0317636 A1 | 12/2008 | Brahim et al. | |
| 2009/0054799 A1 | 2/2009 | Vrtis et al. | |
| 2009/0112115 A1 | 4/2009 | Huang et al. | |
| 2010/0024533 A1 | 2/2010 | Kimura et al. | |
| 2010/0056892 A1 | 3/2010 | Ben-Barak et al. | |
| 2010/0085067 A1 | 4/2010 | Gabriel | |
| 2010/0137733 A1 | 6/2010 | Wang et al. | |
| 2010/0147303 A1* | 6/2010 | Jafari | A61M 16/0051 128/204.23 |
| 2010/0188069 A1 | 7/2010 | Ren et al. | |
| 2010/0198521 A1 | 8/2010 | Haick et al. | |
| 2010/0216175 A1 | 8/2010 | Melker et al. | |
| 2010/0273665 A1 | 10/2010 | Haick et al. | |
| 2011/0015872 A1 | 1/2011 | Haick et al. | |
| 2011/0017587 A1 | 1/2011 | Zhamu et al. | |
| 2011/0143962 A1 | 6/2011 | Chaubron et al. | |
| 2011/0201956 A1 | 8/2011 | Alferness et al. | |
| 2011/0269632 A1 | 11/2011 | Haick et al. | |
| 2011/0283770 A1 | 11/2011 | Hok et al. | |

(56) References Cited

U.S. PATENT DOCUMENTS

| | | |
|---|---|---|
| 2012/0111093 A1 | 5/2012 | Brahim et al. |
| 2012/0126111 A1 | 5/2012 | Chaubron et al. |
| 2012/0156099 A1 | 6/2012 | Zhong et al. |
| 2012/0166095 A1 | 6/2012 | Potyrailo et al. |
| 2012/0203081 A1 | 8/2012 | Leboeuf et al. |
| 2012/0226111 A1 | 9/2012 | Leboeuf et al. |
| 2012/0226112 A1 | 9/2012 | Leboeuf et al. |
| 2012/0245434 A1 | 9/2012 | Haick et al. |
| 2012/0245854 A1 | 9/2012 | Haick et al. |
| 2012/0277794 A1* | 11/2012 | Kountotsis ............ A61B 5/6802 606/234 |
| 2012/0306802 A1 | 12/2012 | McCracken |
| 2012/0326092 A1 | 12/2012 | Haick et al. |
| 2013/0034190 A1 | 2/2013 | Tan et al. |
| 2013/0034910 A1 | 2/2013 | Haick et al. |
| 2013/0059758 A1 | 3/2013 | Haick et al. |
| 2013/0100067 A1 | 4/2013 | Dews |
| 2013/0102018 A1 | 4/2013 | Schentag et al. |
| 2013/0143247 A1 | 6/2013 | Haick et al. |
| 2013/0150261 A1 | 6/2013 | Haick et al. |
| 2013/0165810 A1* | 6/2013 | Saatchi ................. A61B 5/0878 600/537 |
| 2013/0171733 A1 | 7/2013 | Haick et al. |
| 2013/0178756 A1* | 7/2013 | Suzuki .................. A61B 5/0826 600/529 |
| 2013/0211207 A1 | 8/2013 | Joseph et al. |
| 2013/0211852 A1 | 8/2013 | Roizen et al. |
| 2013/0236981 A1 | 9/2013 | Haick et al. |
| 2013/0253358 A1 | 9/2013 | Phillips et al. |
| 2013/0267862 A1* | 10/2013 | Jaffe .................... A61B 5/0816 600/532 |
| 2013/0289368 A1 | 10/2013 | Covington et al. |
| 2013/0331723 A1* | 12/2013 | Hernandez-Silveira ..................... A61B 5/0816 600/529 |
| 2013/0334579 A1 | 12/2013 | Accardi et al. |
| 2014/0018691 A1 | 1/2014 | Mcneill et al. |
| 2014/0041436 A1* | 2/2014 | Knott ................. G01N 33/4972 73/1.06 |
| 2014/0051956 A1 | 2/2014 | Dalene et al. |
| 2014/0094669 A1* | 4/2014 | Jaffe ................. A61M 16/0666 600/324 |
| 2014/0122515 A1 | 5/2014 | Lee et al. |
| 2014/0145735 A1 | 5/2014 | Koester et al. |
| 2014/0171817 A1* | 6/2014 | Blanch .................. A61M 16/00 600/531 |
| 2014/0194703 A1* | 7/2014 | Wondka ............. A61B 5/02055 600/301 |
| 2014/0275597 A1 | 9/2014 | Zhang et al. |
| 2014/0275854 A1* | 9/2014 | Venkatraman .......... A61B 5/318 600/301 |
| 2014/0276168 A1* | 9/2014 | Satya .................... A61B 5/087 600/529 |
| 2014/0294675 A1 | 10/2014 | Melker et al. |
| 2014/0318535 A1* | 10/2014 | Bullock ................. A61M 16/16 128/202.15 |
| 2014/0378790 A1* | 12/2014 | Cohen .................... A61B 5/486 600/309 |
| 2015/0013429 A1 | 1/2015 | Atkin et al. |
| 2015/0038378 A1 | 2/2015 | Cheng et al. |
| 2015/0044710 A1 | 2/2015 | Dasgupta et al. |
| 2015/0065365 A1 | 3/2015 | Lubna |
| 2015/0164373 A1* | 6/2015 | Davis .................... A61B 5/082 600/532 |
| 2015/0196251 A1* | 7/2015 | Cutwater ............. A61B 5/4875 600/301 |
| 2015/0257676 A1 | 9/2015 | Fries |
| 2015/0265184 A1* | 9/2015 | Wondka .................. A61B 5/082 600/532 |
| 2015/0295562 A1 | 10/2015 | Agarwal et al. |
| 2015/0301021 A1 | 10/2015 | Haick et al. |
| 2015/0307936 A1 | 10/2015 | Goldsmith |
| 2015/0309018 A1 | 10/2015 | Goldsmith |
| 2015/0320338 A1* | 11/2015 | Kane .................... A61B 5/0826 600/533 |
| 2015/0335266 A1 | 11/2015 | Cormier |
| 2015/0335267 A1* | 11/2015 | Cormier ................ A61B 5/082 600/532 |
| 2015/0338340 A1* | 11/2015 | Jiang ....................... G01J 3/108 600/532 |
| 2015/0338390 A1 | 11/2015 | Anglin et al. |
| 2015/0351699 A1* | 12/2015 | Addison .............. A61B 5/7221 600/301 |
| 2016/0025675 A1 | 1/2016 | Goldsmith |
| 2016/0054312 A1 | 2/2016 | Goldsmith |
| 2016/0089089 A1 | 3/2016 | Kakkar et al. |
| 2016/0109440 A1* | 4/2016 | Sherwood ............. G01N 27/227 436/501 |
| 2016/0116431 A1 | 4/2016 | Accardi et al. |
| 2016/0150995 A1* | 6/2016 | Ratto ................... A61B 5/0022 600/532 |
| 2016/0157752 A1* | 6/2016 | Cho ..................... A61B 5/7285 600/532 |
| 2016/0192861 A1* | 7/2016 | Gedeon ................ A61B 5/6898 600/532 |
| 2016/0231309 A1 | 8/2016 | Ahmad et al. |
| 2016/0334381 A1 | 11/2016 | King-smith et al. |
| 2016/0370337 A1 | 12/2016 | Blackley |
| 2017/0014043 A1 | 1/2017 | Mcdonnell |
| 2017/0042435 A1 | 2/2017 | Vermeulen et al. |
| 2017/0053068 A1 | 2/2017 | Pillai et al. |
| 2017/0227491 A1 | 8/2017 | Johnson et al. |
| 2017/0307562 A1 | 10/2017 | Goldsmith |
| 2017/0360337 A1 | 12/2017 | Sherwood et al. |
| 2017/0361599 A1 | 12/2017 | Lerner et al. |
| 2017/0365474 A1 | 12/2017 | Pan et al. |
| 2017/0365477 A1 | 12/2017 | Pan et al. |
| 2017/0365562 A1 | 12/2017 | Pan et al. |
| 2018/0035932 A1* | 2/2018 | Massova ............ A61B 5/14551 |
| 2018/0037971 A1 | 2/2018 | Goldsmith |
| 2018/0037985 A1 | 2/2018 | Myers et al. |
| 2018/0328841 A1* | 11/2018 | Graham ............... A61B 5/0836 |
| 2018/0336970 A1 | 11/2018 | Sherwood et al. |
| 2019/0025237 A1 | 1/2019 | Kelly et al. |
| 2019/0178837 A1 | 6/2019 | Xu et al. |
| 2019/0286866 A1 | 9/2019 | Gurt |
| 2020/0166435 A1 | 5/2020 | Sherwood et al. |
| 2020/0191737 A1 | 6/2020 | Sherwood et al. |
| 2021/0148848 A1 | 5/2021 | Kelly et al. |

FOREIGN PATENT DOCUMENTS

| | | |
|---|---|---|
| EP | 1764153 | 3/2007 |
| EP | 1806414 | 7/2007 |
| EP | 3093653 | 11/2016 |
| EP | 3431977 | 1/2019 |
| JP | H11174051 | 7/1999 |
| JP | 2011102747 | 5/2011 |
| JP | 2016022415 | 2/2016 |
| JP | 2016122249 | 7/2016 |
| JP | 2017123912 | 7/2017 |
| WO | 9325142 | 12/1993 |
| WO | 9947905 | 9/1999 |
| WO | 2001070114 | 9/2001 |
| WO | 2008088780 | 7/2008 |
| WO | 2009135070 | 11/2009 |
| WO | 2011109736 | 9/2011 |
| WO | 2013095730 | 6/2013 |
| WO | 2013189502 | 12/2013 |
| WO | 2015191558 | 12/2015 |
| WO | 2016064740 | 4/2016 |
| WO | 2016105464 | 6/2016 |
| WO | 2017218464 | 12/2017 |
| WO | 2018075731 | 4/2018 |

OTHER PUBLICATIONS

Boots, Agnes W. et al., "The Versatile Use of Exhaled Volatile Organic Compounds in Human Health and Disease," J. Breath Res. 6 (2012) 027108 (21 pages).

(56) References Cited

OTHER PUBLICATIONS

"Communication Pursuant to Rules 161(1) and 162 EPC," for European Patent Application No. 15790739.5 dated Jun. 1, 2017 (2 pages).
Deen, David A. et al., "Graphene-Based Quantum Capacitance Wireless Vapor Sensors," IEEE Sensors Journal, vol. 14, No. 5, May 2014, pp. 1459-1466 (8 pages).
Droscher, S. et al., "Quantum Capacitance and Density of States of Graphene," Phys. Scr. T146 (2012) 014009, pp. 1-5 (5 pages).
Ebrish, M. A. et al., "Dielectric Thickness Dependence of Quantum Capacitance in Graphene Varactors with Local Metal Back Gates," Device Research Conference, 2012 (2 pages).
"FDC1004 4-Channel Capacitance-to-Digital Converter for Capacitive Sensing Solutions," Data Sheet SNOSCY5B Texas Instruments Aug. 2014—Revised 2015 (24 pages).
"FDC1004EVM User Guide," Literature No. SNAU163C, Texas Instruments August 2014—Revised Oct. 2016 (46 pages).
Fisher, James P. et al., "Central Sympathetic Overactivity: Maladies and Mechanisms," Autonomic Neuroscience 148.1 (2009): 5-15 (11 pages).
Georgakilas, Vasilios et al., "Functionalization of Graphene: Covalent and Non-Covalent Approaches, Derivatives and Applications," Chemical Reviews, 2012, 14:112(11), pp. 6156-6214.
Hu, Yuhai et al., "Chemically Functionalized Graphene and Their Applications in Electrochemical Energy Conversion and Storage," Advances in Graphene Science, Chapter 7, 2013, pp. 161-190 (30 pages).
"International Preliminary Report on Patentability," for PCT Application No. PCT/US2015/056243 dated May 4, 2017 (8 pages).
"International Search Report and Written Opinion," for PCT Application No. PCT/US2015/056243, dated Jan. 26, 2016 (12 pages).
"International Search Report and Written Opinion," for PCT Application No. PCT/US2017/037144 dated Oct. 6, 2017 (11 pages).
Koester, Steven J. "Using the Quantum Capacitance in Graphene to Enable Varactors for Passive Wireless Sensing Applications," 2011 IEEE Sensors Proceedings, pp. 994-997, 2011 (4 pages).
Li, Xiao et al., "Digital Health: Tracking Physiomes and Activity Using Wearable Biosensors Reveals Useful Health-Related Information," PLoS Biology 15.1 (2017): e2001402 (30 pages).
"Mechanical Data," DGS (S-PDSO-G10) DSC0010B Package Outline, Example Board Layout, and Stencil Design. Texas Instruments 2016 (5 pages).
Nakhleh, Morad K. et al., "Diagnosis and Classification of 17 Diseases from 1404 Subjects via Pattern Analysis of Exhaled Molecules," ACS Nano 2017, 11, 112-125 (14 pages).
"Nano Mobile Healthcare Inc.," Company Profile on Reuters.com URL <http://www.reuters.com/finance/stocks/companyProfile?symbol=VNTH.PK> accessed March 17, 2017 (2 pages).
"Package Materials Information," Tape and Reel Information and Box Dimensions. Texas Instruments Feb. 13, 2016 (2 pages).
"Package Option Addendum," Packaging Information for FDC1004DGSR, DGST, DSCJ, DSCR and DSCT Devices. Texas Instruments May 2015 (2 pages).
"Response to Communication Pursuant to Rules 161(1) and 162 EPC," for European Patent Application No. 15790739.5 filed with the EPO Dec. 8, 2017 (14 pages).
"Standard Terms and Conditions for Evaluation Modules," Texas Instruments 2016 (5 pages).
Wang, David, "FDC1004: Basics of Capacitive Sensing and Applications," Application Report SNOA927, Texas Instruments Dec. 2014 (12 pages).
Communication Pursuant to Article 94(3) EPC for European Patent Application No. 18180455.0 dated Feb. 11, 2019 (6 pages).
Deen, David A. et al., "Graphene-Based Quantum Capacitance Wireless Vapor Sensors," IEEE Sensors Journal, vol. 14, No. 5, May 2014 (8 pages).
Ebrish, M.A. et al., "Operation of multi-finger graphene quantum capacitance varactors using planarized local bottom gate electrodes," Applied Physics Letters, vol. 100, No. 14, Apr. 2012 (4 pages).

European Search Report for European Patent Application No. 18180455.0 dated Dec. 2018 (5 pages).
First Office Action for Chinese Patent Application No. 201580056417.2 dated Feb. 11, 2019 (13 pages) with English summary.
International Preliminary Report on Patentability for PCT Application No. PCT/US2018/037144 dated Dec. 27, 2018 (7 pages).
Ma, Rui et al., "Acetone Sensing Using Graphene Quantum Capacitance Varactors," IEEE Sensors, Oct. 30, 2016 (3 pages).
Non-Final Office Action for U.S. Appl. No. 14/883,895 dated Feb. 15, 2019 (17 pages).
Opera, A. et al., "Integrated Temperature, Humidity and Gas Sensors on Flexible Substrates for Low-Power Applications," Sensors, Jan. 1, 2007 (4 pages).
Response to Advisory Action dated Dec. 3, 2018, for U.S. Appl. No. 14/883,895, submitted via EFS-Web on Dec. 14, 2018, 11 pages.
Final Office Action for U.S. Appl. No. 14/883,895 dated Sep. 14, 2018 (16 pages).
International Search Report and Written Opinion for PCT Application No. PCT/US2018/033166 dated Oct. 2, 2018 (12 pages).
Response to Final Rejection dated Sep. 14, 2018, for U.S. Appl. No. 14/883,895, submitted via EFS-Web on Nov. 7, 2018, 11 pages.
Tripathi, Kumud M. et al., "Recent Advances in Engineered Graphene and Composites for Detection of Volatile Organic Compounds (VOCs) and Non-Invasive Diseases Diagnosis," Carbon 110 (2016)97-129 (34 pages).
Ebrish, M. A. et al., "Operation of Multi-Finger Graphene Quantum Capacitance Varactors using Planarized Local Bottom Gate Electrodes," Applied Physics Letters, A I P Publishing LLC, 2012 (5 pages).
European Search Report for Dutch Patent Application No. 2019492 dated Apr. 12, 2018 (10 pages).
International Search Report and Written Opinion for PCT Application No. PCT/US2017/057318 dated Feb. 6, 2018 (14 pages).
Ma, Rui et al., "Acetone Sensing Using Graphene Quantum Capacitance Varactors," 2016 IEEE Sensors, Orlando, FL, 2016 (3 pages).
Non-Final Office Action for U.S. Appl. No. 14/883,895 dated Apr. 30, 2018 (37 pages).
Oprea, A. et al., "Integrated Temperature, Humidity and Gas Sensors on Flexible Substrates for Low-Power Applications," 007 IEEE Sensors, Atlanta, GA, 2007, pp. 158-161 (4 pages).
Response to Non-Final Office Action for U.S. Appl. No. 14/883,895, dated Apr. 30, 2018 and filed with the USPTO Jul. 2, 2018 (18 pages).
Communication Pursuant to Article 94(3) EPC for European Patent Application No. 18180455.0 dated Jul. 15, 2019 (5 pages).
Final Office Action for U.S. Appl. No. 14/883,895 dated Jul. 18, 2019 (19 pages).
International Preliminary Report on Patentability for PCT Application No. PCT/US2017/057318 dated May 2, 2019 (11 pages).
Response to Communication Pursuant to Article 94(3) EPC for European Patent Application No. 18180455.0 filed Jun. 6, 2019 (44 pages).
Response to Communication Pursuant to Rules 161(1) and 162 EPC for European Patent Application No. 17733246.7 filed May 29, 2019 (22 pages).
Response to Non-Final Rejection dated Feb. 15, 2019 for U.S. Appl. No. 14/883,895, submitted via EFS-Web on May 10, 2019, 10 pages.
Communication Pursuant to Article 94(3) EPC for European Patent Application No. 15790739.5 dated Dec. 17, 2019 (5 pages).
Communication Pursuant to Article 94(3) EPC for European Patent Application No. 18180455.0 dated Dec. 20, 2019 (3 pages).
International Preliminary Report on Patentability for PCT Application No. PCT/US2018/033166 dated Nov. 28, 2019 (8 pages).
Non-Final Office Action for U.S. Appl. No. 14/883,895 dated Nov. 27, 2019 (16 pages).
Non-Final Office Action for U.S. Appl. No. 15/982,506 dated Dec. 11, 2019 (41 pages).
Response to Advisory Action dated Oct. 11, 2019 for U.S. Appl. No. 14/883,895, submitted via EFS-Web on Oct. 16, 2019, 10 pages.
Response to Communication Pursuant to Article 94(3) EPC for European Patent Application No. 18180455.0 filed Nov. 12, 2019 (9 pages).

(56) References Cited

OTHER PUBLICATIONS

Response to Communication Pursuant to Rules 161(1) and 162 EPC for European Patent Application No. 17794832.0 filed Dec. 6, 2019 (9 pages).
Response to Final Rejection dated Jul. 18, 2019 for U.S. Appl. No. 14/883,895, submitted via EFS-Web on Sep. 18, 2019, 10 pages.
Second Office Action for Chinese Patent Application No. 201580056417.2 dated Sep. 25, 2019 (6 pages) No English Translation.
Non-Final Office Action for U.S. Appl. No. 15/621,103 dated Feb. 21, 2020 (58 pages).
Office Action for Japanese Patent Application No. 2019-517196 dated Feb. 4, 2020 (10 pages) with English Translation.
Response to Non-Final Rejection dated Dec. 11, 2019 for U.S. Appl. No. 15/982,506, submitted via EFS-Web on Feb. 25, 2020, 13 pages.
Response to Non-Final Rejection dated Nov. 27, 2019 for U.S. Appl. No. 14/883,895 submitted via EFS-Web on Feb. 5, 2020, 9 pages.
Third Office Action for Chinese Patent Application No. 201580056417.2 dated Feb. 18, 2020 (6 pages) No English Translation.
Final Office Action for U.S. Appl. No. 15/621,103 dated Jun. 8, 2020 (21 pages).
Response to Non-Final Rejection dated Feb. 21, 2020 for U.S. Appl. No. 15/621,103, submitted via EFS-Web on May 20, 2020.
Notice of Allowance for U.S. Appl. No. 16/037,218 dated Jul. 31, 2020 (20 pages).
Office Action for Japanese Patent Application No. 2019-520955 dated Jul. 14, 2020 (10 pages) with English Translation.
Response to Communication Pursuant to Rules 161(1) and 162 EPC for European Patent Application No. 18731579.1 filed Jul. 17, 2020 (19 pages).
Response to Final Rejection dated Jun. 8, 2020 for U.S. Appl. No. 15/621,103, submitted via EFS-Web on Aug. 20, 2020, 16 pages.
Response to Final Rejection dated May 1, 2020 for U.S. Appl. No. 14/883,895, submitted via EFS-Web on Jul. 15, 2020, 12 pages.
Response to Non-Final Rejection dated Apr. 29, 2020 for U.S. Appl. No. 16/037,218, submitted via EFS-Web on Jul. 15, 2020, 7 pages.
Bhadra, Sharmista et al., "Non-destructive detection offish spoilage using a wireless basic volatile sensor," Talanta, vol. 134, Dec. 25, 2014 pp. 718-723 (6 pages).
Ebrish, Mona A. et al., "Effect of Noncovalent Basal Plane Functionalization of the Quantum Capacitance in Graphene," ACS Appl. Mater. Interfaces 2014, 6, 10296-10303 (8 pages).
Final Office Action for U.S. Appl. No. 14/883,895 dated May 1, 2020 (19 pages).
International Search Report and Written Opinion for PCT Application No. PCT/US2019/063324 dated Mar. 27, 2020 (17 pages).
International Search Report and Written Opinion for PCT Application No. PCT/US2019/065981 dated Mar. 16, 2020 (14 pages).
Koester, Steven J. "High Quality Factor Graphene Varactors for Wireless Sensing Applications," Applied Physics Letters 99, 163105 (2011), 3 pages.
Navaneethan, Udayakumar et al., "Volatile Organic Compounds in Bile Can Diagnose Malignant Biliary Strictures in the Setting of Pancreatic Cancer: A Preliminary Observation," Gastrointest Endosc. Dec. 2014;80(6):1038-45 (8 pages).
Non-Final Office Action for U.S. Appl. No. 16/037,218 dated Apr. 29, 2020 (46 pages).
Notice of Allowance for U.S. Appl. No. 15/982,506 dated May 7, 2020 (17 pages).
Olson, Eric J. et al., "Capacitive Sensing of Intercalated H2O Molecules Using Graphene," ACS Appl. Mater. Interfaces 2015, 7(46), 25804-25812 (29 pages).
Response to Communication Pursuant to Article 94(3) EPC for European Patent Application No. 15790739.5 filed Apr. 24, 2020 (16 pages).
Response to Communication Pursuant to Article 94(3) EPC for European Patent Application No. 18180455.0 filed Apr. 21, 2020 (24 pages).
Zhang, Yao et al., "Capacitive Sensing of Glucose in Electrolytes using Graphene Quantum Capacitance Varactors," ACS Appl. Mater. Interfaces 2017, 9, 38863-38869 (7 pages).
Zhang, Yao et al., "Glucose Sensing with Graphene Varactors," IEEE Sensors, SENSORS 2016—Proceedings, Orlando, FL 2016 (3 pages).
Zhen, Xue et al., "Noncovalent Monolayer Modification of Graphene Using Pyrene and Cyclodextrin Receptors for Chemical Sensing," ACS Applied Nano Materials 2018, vol. 1, No. 6 pp. 2718-2726 (9 pages).
"Office Action," for Japanese Patent Application No. 2019-520955 dated Feb. 9, 2021 (11 pages) with English Translation.
"Response to Communication Pursuant to Article 94(3) EPC," for European Patent Application No. 18731579.1 filed Mar. 15, 2021 (12 pages).
"Response to Non-Final Rejection," dated Oct. 23, 2020 for U.S. Appl. No. 15/621,103, submitted via EFS-Web on Jan. 22, 2021, 17 pages.
Communication Pursuant to Article 94(3) EPC for European Patent Application No. 18731579.1 dated Nov. 10, 2020 (5 pages).
First Office Action for Chinese Patent Application No. 201780030595.7 dated Nov. 2, 2020 (12 pages) with English Summary.
Non-Final Office Action for U.S. Appl. No. 15/621,103 dated Oct. 23, 2020 (27 pages).
Office Action for Japanese Patent Application No. 2019-563876 dated Nov. 4, 2020 (3 pages) No English Translation.
Response to Final Rejection dated Jun. 8, 2020 and Advisory Action dated Sep. 4, 2020, for U.S. Appl. No. 15/621,103, submitted via EFS-Web on Oct. 8, 2020, 16 pages.
"Extended European Search Report," for European Patent Application No. 20214733.6 dated Apr. 21, 2021 (11 pages).
"Final Office Action," for U.S. Appl. No. 15/621,103 dated Apr. 22, 2021 (20 pages).
"International Preliminary Report on Patentability," for PCT Application No. PCT/US2019/063324 dated Jun. 10, 2021 (10 pages).
"Non-Final Office Action," for U.S. Appl. No. 14/883,895 dated May 20, 2021 (34 pages).
"Office Action," for Chinese Patent Application No. 201780065376.2 dated Apr. 27, 2021 (10 pages) with English Summary.
Zhang, Xu et al., "A Wide Measurement Range and Fast Update Rate Integrated Interface for Capacitive Sensors Array," IEEE Transactions on Circuits and Systems—1: Regular Papers, Vo. 61, No. 1, Jan. 2014, pp. 2-11 (10 pages).
"International Preliminary Report on Patentability," for PCT Application No. PCT/US2019/065981 dated Jul. 1, 2021 (8 pages).
"New Summons to Attend Oral Proceedings," for European Patent Application No. 18731579.1 dated Jul. 12, 2021 (6 pages).
"Response to Final Rejection," dated Apr. 22, 2021 and the Advisory Action dated Jul. 8, 2021 for U.S. Appl. No. 15/621,103, submitted via EFS-Web on Jul. 12, 2021, 13 pages.
"Response to Final Rejection," dated Apr. 22, 2021 for U.S. Appl. No. 15/621,103, submitted via EFS-Web on Jun. 22, 2021, 13 pages.
"Second Office Action," for Chinese Patent Application No. 201780030595.7 dated Jun. 17, 2021 (8 pages), with English Summary.
"Summons to attend oral proceedings pursuant to Rule 115(1) EPC," for European Patent Application No. 18731579.1 dated Jul. 1, 2021 (6 pages).

\* cited by examiner

GAS SAMPLING DEVICE

This application claims the benefit of U.S. Provisional Application No. 62/411,383, filed Oct. 21, 2016, the contents of which are herein incorporated by reference in their entireties.

FIELD OF THE TECHNOLOGY

Embodiments herein relate to gas sampling devices, systems and methods.

BACKGROUND

The accurate detection of diseases can allow clinicians to provide appropriate therapeutic interventions. Further, the early detection of diseases can lead to better treatment outcomes. Diseases can be detected using many different techniques including analyzing tissue samples, analyzing various bodily fluids, diagnostic scans, and the like.

Some disease states result in the increased or decreased production of specific chemical compounds. As such, the detection of these chemical compounds in gas samples or patterns of the same can allow for the early detection of particular disease states.

SUMMARY

The technology disclosed herein relates to, in part, a gas sampling device. According to some aspects, the gas sampling device has a housing defining an airflow aperture, a gas testing chamber and an airflow pathway extending from the airflow aperture to the gas testing chamber. The housing also defines a sensor receptacle configured to removably hold a disposable sensor test strip within the gas testing chamber and a docking structure configured to be received by a docking station.

In addition or alternatively, the gas sampling device has a one-way valve disposed across the airflow pathway between the airflow aperture and the gas testing chamber. In addition or alternatively, the gas sampling device has a conditioning element in communication with the airflow pathway between the airflow aperture and the gas testing chamber. In addition or alternatively, the conditioning element is a filter element disposed across the airflow pathway. In addition or alternatively, the filter element is at least one of the group consisting of: a desiccant, an oxidizing agent, and a reducing agent. In addition or alternatively, the conditioning element is a heating element disposed along the airflow pathway. In addition or alternatively, the conditioning element is a gas source in fluid communication with the gas testing chamber. In addition or alternatively, the conditioning element is a heating element disposed along a portion of the airflow pathway. In addition or alternatively, the heating element is configured to heat at least 90% of interior surfaces of portions of the housing defining the airflow pathway.

In addition or alternatively, the gas sampling device has a sensor coupled to the housing. In addition or alternatively, the sensor is disposed in the airflow pathway. In addition or alternatively, the sensor is a carbon dioxide sensor. In addition or alternatively, the sensor is a humidity sensor. In addition or alternatively, the sensor is a temperature sensor.

In addition or alternatively, the sensor is disposed on an exterior surface of the housing. In addition or alternatively, the sensor is a heart rate sensor. In addition or alternatively, the sensor is a temperature sensor.

In addition or alternatively, the housing of the gas sampling device further defines an inhalation inlet and an inhalation pathway extending from the airflow aperture to the inhalation inlet and a VOC-filter is disposed across the inhalation pathway. In addition or alternatively, the gas sampling device has a one-way valve disposed across the inhalation pathway between the inhalation inlet and the airflow aperture.

According to some other aspects of the technology disclosed herein, a system for collecting patient data is disclosed. The system has a gas sampling device having a housing and a docking station. The gas sampling device defines a gas testing chamber, an airflow aperture, and an airflow pathway extending from the airflow aperture to the gas testing chamber. The gas sampling device also defines a sensor receptacle configured to removably hold a disposable sensor test strip within the gas testing chamber. The docking station is configured to receive the gas sampling device, and has a reading device having communication hardware to wirelessly receive data through the housing of the gas sampling device.

In addition or alternatively, the system has a plurality of disposable sensor test strips each configured to be removably received by the sensor receptacle and the gas testing chamber. In addition or alternatively, each of the plurality of disposable sensor test strips has an identification code. In addition or alternatively, each of the plurality of disposable sensor test strips has an array of discrete passive sensor circuits.

In addition or alternatively, the docking station has a proximity sensor configured to detect the gas sampling device. In addition or alternatively, the communication hardware has a near field electrode configured to receive patient data from a passive electrical circuit. In addition or alternatively, the reading device also has networking hardware configured to transmit data over a network. In addition or alternatively, the system has a disposable mouthpiece configured to removably couple to the gas sampling device about the airflow aperture. In addition or alternatively, the disposable mouthpiece has an airflow pathway liner configured to abut the airflow pathway and the airflow aperture.

Some aspects of the technology disclosed herein relate to a method of analyzing patient data. A disposable sensor test strip is received by a gas testing chamber defined by a housing of a gas sampling device. The gas sampling device is docked to a docking station having a reading device. Baseline data is read from the disposable sensor test strip by the reading device through the housing of the gas sampling device. The gas sampling device is undocked from the docking station after reading the baseline data. A gas sample is received by the gas testing chamber such that the gas sample is in contact with the disposable sensor test strip. The gas sampling device is docked to the docking station after receiving the gas sample. Gas sample data is read from the disposable sensor test strip by the reading device, through the housing of the gas sampling device.

In addition or alternatively, the baseline data is removed from the tested gas data by the docking station to obtain adjusted data. In addition or alternatively, the adjusted data is compared to known data indicative of a disease by the docking station. In addition or alternatively, the adjusted data is sent from the docking station to a remote system over a network, and comparing the adjusted data to known data indicative of a plurality of diseases by the remote system. In addition or alternatively, baseline data is read by identifying a defect in the disposable sensor test strip by the docking station. In addition or alternatively, the baseline data and the tested gas data is transmitted over a network, by the docking station, to a remote system. In addition or alternatively, the gas sampling device provides visual notification that it is ready to receive a gas sample.

BRIEF DESCRIPTION OF THE DRAWINGS

The current technology may be more completely understood and appreciated in consideration of the following detailed description of various embodiments of the current technology in connection with the accompanying drawings.

DETAILED DESCRIPTION

Figure 1:
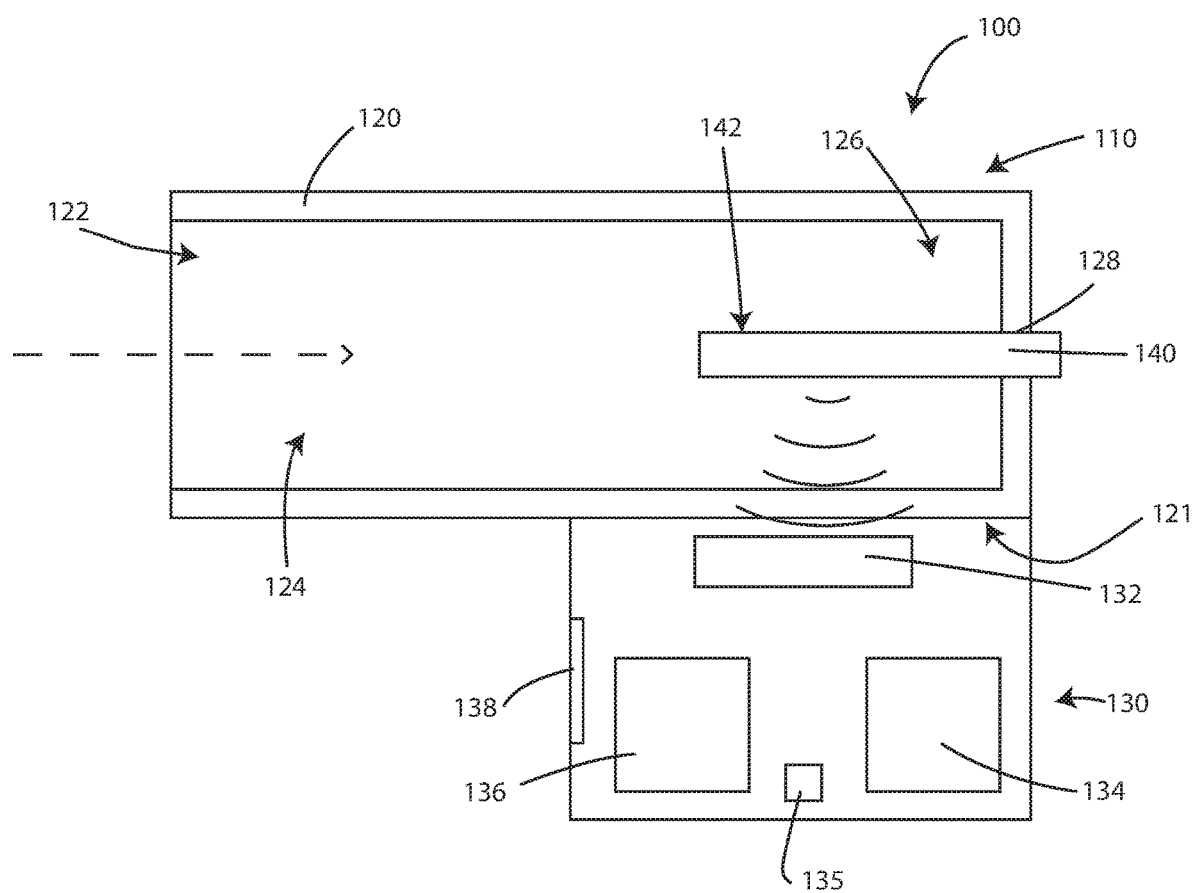
FIG. 1 is a schematic cross-sectional view of a system consistent with the technology disclosed herein.

The embodiments described herein are not intended to be exhaustive or to limit the currently described technology to the precise forms disclosed in the following detailed description. Rather, the embodiments are chosen and described so that others skilled in the art can appreciate and understand the principles and practices.

All publications and patents mentioned herein are hereby incorporated by reference. The publications and patents disclosed herein are provided solely for their disclosure. Nothing herein is to be construed as an admission that the inventor(s) are not entitled to antedate any publication and/or patent, including any publication and/or patent cited herein.

Disposable test strips (or sensor elements) can be useful for detecting analytes in gas samples allowing for the convenient and early detection of particular disease states. In particular, discrete binding detectors can be disposed on test strips and can detect chemical compounds in gas samples and/or patterns of chemical compounds in gas samples which can then be used to identify a possible disease state or other condition through pattern matching algorithms. Aspects of exemplary disposable test strips are described in U.S. Publ. Pat. Appl. No. 2016/0109440, the content of which is herein incorporated by reference.

However, there are issues associated with the practical use of such test strips. In particular, it can be challenging to both conveniently obtain a breath sample from a patient and then process that same breath sample. A handheld device for obtaining a gas sample can be ideal as it can be easily manipulated by a care provider and can be used even by patients that are relatively infirm and may have trouble interfacing with a larger, more bulky device. However, some devices used for actually reading data from disposable testing elements, once a gas sample has been obtained, can be relatively large making handheld use difficult or impractical. Further, storing a gas to be analyzed, or conveying the gas sample from one device to another may degrade the analytical value of the gas sample, which makes dividing the system up into multiple discrete elements difficult.

Embodiments herein relate to systems, devices, and related methods associated with collecting gas samples, such as the exhaled breath of a patient. Specifically, some systems and devices disclosed herein can be used to collect a gas sample from a patient with a first device (such as a handheld device) that holds a disposable test strip for detection of chemical compounds, including but not limited to volatile organic compounds and/or patterns of the same. The handheld device can then be docked with a second device (or docking station) which includes circuitry to receive or read data from the disposable test strip that can, in turn, can be used to identify disease states such as cancer, cardiac diseases, infections, multiple sclerosis, Alzheimer's disease, Parkinson's disease, and the like. In some embodiments, the first and second devices can be cleaned and/or sterilized as necessary and then reused with new disposable test strips for additional testing with same or different patients or test subjects. In some embodiments, graphene-based sensors are included on disposable sensor test strips that can be used in conjunction with breath analysis systems in order to accurately sense very low concentrations of analytes and/or analyte patterns in order to allow the rapid detection of disease states with high sensitivity. Aspects of some exemplary embodiments will now be described in greater detail with reference to the figures.

FIG. 1 is a schematic cross-sectional view of an example system 100 consistent with the technology disclosed herein. It will be appreciated that this schematic view has been simplified for ease of illustration and that embodiments of systems and devices herein can include various features not shown in FIG. 1. In addition, some embodiments of systems and devices herein may lack various features shown in FIG. 1. The system 100 is generally configured for collecting a gas sample and communicating data associated with the gas sample. The system 100 has a gas sampling device 110 and a docking station 130.

The gas sampling device 110 is generally configured to collect a gas sample and facilitate testing of the gas sample to generate data. In some embodiments, the gas sampling device 110 can be configured as a handheld device. In such cases, the gas sampling device can be configured to be held in the hand of a care provider, a patient, or both, during certain steps of its use, while also being configured to be held or otherwise positioned in association with the docking station 130 during certain steps of its use.

In some embodiments, the gas sampling device 110 is configured to receive a gas sample, such as exhaled breath, from a patient and direct the gas sample to a testing location. The gas sampling device 110 generally has a housing 120 defining an airflow aperture 122, a gas testing chamber 126, a sensor receptacle 128, an airflow pathway 124, and a docking structure 121.

When receiving a gas sample, the gas (such as breath from a patient), can pass into the gas sampling device 110 through the airflow aperture 122, through the airflow pathway 124, into the gas testing chamber 126 and into contact with one or more measurement zones 142 of a disposable sensor test strip 140, and then out the end of the gas testing chamber 126 through the sensor receptacle 128, or through a separate exhaust port (not shown in this view). While this view depicts contact between the sensor receptacle 128 and the disposable sensor test strip 140, it will appreciated that there can be segments or areas where the sensor receptacle 128 and the disposable sensor test strip 140 do not contact or do not create sealing contact, thus allowing for a path for the gas to flow out through the sensor receptacle 128.

While in FIG. 1, the airflow pathway 124 is shown to be approximately the same size as the interior space of the housing 120, it will be appreciated that this is simply for ease of illustration and that the size of the airflow pathway 124 can be, in many cases, much smaller than the entire interior size of the housing 120, allowing for room for other components within the interior of the housing 120, such as other components described herein including, but not limited to, sensors, a power source, processing devices, communication hardware, conditioning elements, and the like.

The housing 120 can be constructed of a variety of materials and combinations of materials. The housing 120 can be a single cohesive structure or can be constructed of multiple components that are coupled to form the housing 120. As an illustrative example, a portion of the housing 120 that defines the airflow pathway 124 can be coupled to the portion of the housing 120 that defines the airflow aperture 122. The portion of the housing 120 that defines the airflow pathway 124 can include a conduit or tube with various different cross-sectional sizes and shapes. The conduit or tube can be formed from various materials including, but not limited to, polymers, metals, ceramics, glass, composites or the like. In some embodiments, surfaces lining the airflow pathway 124 can be coated with materials to provide various desirable functional properties.

The airflow aperture 122 is generally configured to provide an input for the gas sample at the housing 120. In some embodiments the airflow aperture 122 is configured to be in fluid communication with a patient's mouth, although in some other embodiments a protective liner can be used to provide a barrier between the patient's mouth and the housing, which will be described in more detail, below.

The airflow pathway 124 generally is configured to direct the gas input at the airflow aperture 122 to the gas testing chamber 126. As such, the airflow pathway 124 generally extends from the airflow aperture 122 to the gas testing chamber 126. The airflow pathway 124 can have a cross-sectional area that is substantially the same along the length of the airflow pathway or it can vary. In some embodiments, the gas testing chamber 126 can have different interior dimensions (e.g., height, width, etc.) than the airflow pathway leading to it.

The gas testing chamber 126 defines a testing location for the gas sample. In various embodiments, the gas testing chamber 126 is configured to receive a measurement zone 142 of a disposable sensor test strip 140. Accordingly, the sensor receptacle 128 defined by the housing 120 is generally configured to removably retain the disposable sensor test strip 140 within the gas testing chamber 126. In various embodiments the sensor receptacle 128 is configured to slidably receive the disposable sensor test strip 140 that is manually inserted by a user. In some embodiments, the disposable sensor test strip 140 can be inserted with its long (or major) axis parallel to the long (or major) axis of the housing 120. However, in other embodiments, the disposable sensor test strip 140 can be inserted with its long (or major) axis positioned differently with respect to the long (or major) axis of the housing 120, such as perpendicular. Example sensor test strips will be described in more detail, below.

While FIG. 1 depicts the test strip located approximately in the middle of the gas sampling device 110 (top to bottom with regard to the perspective of the figure), it will be appreciated that the test strip can be positioned biased toward the top or the bottom, to be closer to an exterior surface of the housing 120 or gas sampling device 110. In some cases this can facilitate easier wireless reading of the disposable sensor strip by the docking station while the disposable sensor strip is still held within the housing. In some embodiments, the disposable sensor strip can be positioned less than 5 cm, 4 cm, 3 cm, 2 cm, 1 cm, 0.5 cm, 0.2 cm or less from exterior surface (or exterior wall) of the housing 120.

The docking station 130 is generally configured to collect data generated from testing the gas sample. The docking station 130 has a reading device 132 having communication hardware to wirelessly receive data through the housing of the gas sampling device 110. In many embodiments the reading device 132 of the docking station 130 is configured to wirelessly receive data from the disposable sensor test strip 140. In various embodiments, the reading device 132 can also be configured to wirelessly receive baseline data through the housing of the gas sampling device 110—from the disposable sensor test strip 140—where the term "baseline data" is defined as data collected before exposure of the disposable sensor test strip 140 to the gas sample or the patient or test subject. In some cases the baseline data can reflect conditions of whatever gas happens to be the testing chamber prior to obtaining a gas sample of a patient. However, in other embodiments, ambient air can purposefully be pushed through the testing chamber, and/or a particular reference gas sample of known composition can be put into the testing chamber for purposes of generating baseline data. The communication hardware of the reading device 132 can be capable of near field communication with the disposable sensor test strip 140. In some embodiments the communication hardware of the reading device 132 is a near field electrode or near field reading circuit that is configured to receive patient data from a passive electrical circuit, such as by detecting a resonant frequency of an LRC resonator circuit and/or changes to the same. Details of how the reading device 132 can read the data will be described in more detail with respect to FIG. 3.

In some embodiments the docking station has a proximity sensor that is configured to detect when the gas sampling device 110 is in sufficient proximity to the docking station 130 to collect data. And, although not currently depicted, in some embodiments the disposable sensor test strip 140 can have identifying information disposed thereon, other than the baseline or patient sample data, that can be read by a docking station or another device such as an identification code, radio frequency identification (RFID) tag, barcode, serial or id numbers, or other indicia. In such embodiments the docking station 130 (FIG. 1) can be configured to read, collect, save, and/or potentially transmit that identification data.

The docking station 130 is generally configured to be a docking location for the gas sampling device 110. The docking station 130 is generally configured to physically receive the gas sampling device 110. The docking station 130 can receive the gas sampling device 110 through a variety of structures and configurations that will be appreciated by those having ordinary skill in the art. In various embodiments the docking station 130 and the docking structure 121 of the gas sampling device 110 have a mating configuration by which the docking station 130 receives the docking structure 121 of the gas sampling device 110. In some such embodiments the docking station 130 and the docking structure 121 define an interference fit. However, in other embodiments, the docking station 130 can simply rest upon or in the docking structure 121. In some embodiments the docking station 130 and the docking structure 121 are configured to position the disposable sensor test strip 140 and the reading device 132 in sufficient proximity to accommodate transmission of data between the reading device 132 and disposable sensor test strip 140. In some embodiments the docking station and the docking structure are configured to position the disposable sensor test strip 140 and the reading device 132 within 6 cm, 5 cm, 4 cm, 3 cm, or 2 cm of each other, or even within 1 cm of each other.

The docking station 130 can have various additional components. In some embodiments the docking station 130 has a processor 136 and memory 135. The processor 136 and memory 135 can be configured to process and store data obtained from tested the gas sample. For example, the memory 135 can store baseline data locally and the processor 136 can be configured to remove collected baseline data from the tested gas data to obtain adjusted data. Such adjusted data can remove some impact of the ambient environment on the tested gas data. In another example, the processor can be configured to compare the adjusted data (or, in some embodiments the tested gas data) to known data indicative of one or more diseases. Such a comparison can be used to identify the presence of a particular disease using a comparative algorithm. In yet another example, the processor of the docking station 130 can be configured to identify a defect in the disposable sensor test strip 140. Example defects can include manufacturing defects and/or premature exposure to ambient gases. The docking station 130 can be configured to collect, save, and potentially transmit records of such defects.

The docking station 130 has networking hardware 134 in various embodiments. The networking hardware 134 can be configured to transmit data over a network to a remote system, including a cloud-based system. In some implementations the remote system can be a hospital, clinic, laboratory, or other location. In some embodiments the networking hardware 134 is configured to transmit data generated from testing the gas sample. The networking hardware 134 is configured to transmit baseline data in some embodiments. The networking hardware is configured to transmit adjusted data in some embodiments. In some embodiments the remote system analyzes the data it receives. For example, in some embodiments the remote system is configured to compare the adjusted data to known data indicative of a plurality of diseases. That comparison can identify the presence of a particular disease.

In some embodiments the docking station 130 has a user interface 138. The user interface 138 can be configured to communicate information to a user. For example, the user interface 138 can be configured to communicate an active data transmission, such as a data transmission between the docking station 130 and the gas sampling device 110 and/or between the docking station 130 and a network. In some embodiments the user interface 138 can be configured to communicate information about the current stage of the testing process, progress of the same, or what steps are next or what actions are required. For example, in some cases the user interface 138 can be configured to communicate that that the gas sampling device 110 is ready to receive a gas sample or that the docking station 130 has finished reading data from the gas sampling device 110. The user interface 138 can also be configured to communicate a defect in the sensor test strip. The user interface 138 can be configured to communicate through visual notification, audio notification, and the like. As a specific example, a flashing light can be used to indicate that the docking station 130 is transmitting data. The user interface 138 can include a light source such as an LED or similar light emitting device.

One example approach to using the system depicted in FIG. 1 will now be described. A disposable sensor test strip 140 is inserted into the gas sampling device 110 such that it is received by the gas testing chamber 126 defined by a housing of a gas sampling device. The gas sampling device 110 having the disposable sensor test strip 140 is docked to the docking station 130, and the reading device 132 of the docking station 130 reads baseline data from the disposable sensor test strip 140 through the housing 120 of the gas sampling device 110. The gas sampling device 110 is undocked from the docking station 130 after reading the baseline data, and a gas sample is received by the gas testing chamber such that the gas sample is brought into contact with the disposable sensor test strip 140. For example, the gas sampling device 110 may be physically grasped by a care provider and removed from the docking station 130 and physically handed to a patient or test subject who may then blow into the gas sampling device 110 to provide the gas sample to be analyzed. In other cases, the gas sampling device 110 may be held by the care provider instead of being held by the patient or test subject. The gas sampling device 110 can then be docked to the docking station 130 after receiving the gas sample, and the data from the tested gas is read from the disposable sensor test strip 140 by the reading device 132, wherein the comparison data is read through the housing 120 of the gas sampling device 110. In various embodiments the disposable sensor test strip 140 is configured to be single-use. As such, the disposable sensor test strip 140 can be disposed of following the collection of sample gas data from the disposable sensor test strip 140. Various other methods of using the system depicted in FIG. 1 are also contemplated.

Figure 2:
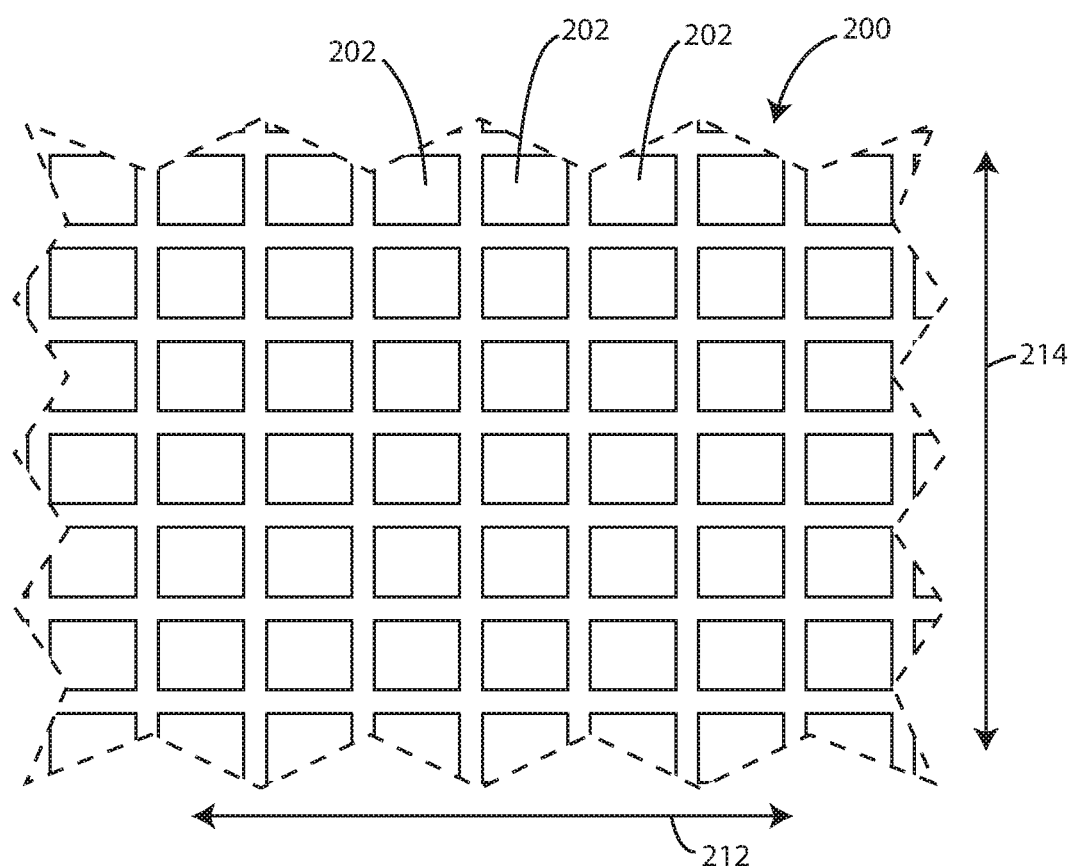
FIG. 2 is a schematic diagram of a portion of a disposable sensor test strip in accordance with various implementations of the technology disclosed herein.

In a variety of embodiments, the gas sampling device 110 described above has a sensor receptacle 128 and a gas testing chamber 126 that are configured to removably receive one or more disposable sensor test strips. FIG. 2 is a schematic diagram of a measurement zone 200 of an example disposable sensor test strip 140 (see FIG. 1) in accordance with various implementations of the technology disclosed herein. An array of discrete gas sensor circuits, each having a discrete binding detector 202, is disposed within the measurement zone 200. In some embodiments, the discrete binding detectors 202 can be heterogeneous in that they are all different from one another in terms of their binding behavior or specificity with regard to analytes. In some embodiments, some discrete binding detectors 202 can be duplicated for validation purposes, but are otherwise heterogeneous from other discrete binding detectors.

While the discrete binding detectors 202 of FIG. 2 are shown as boxes organized into a grid, it will be appreciated that the discrete binding detectors can take on many different shapes (including, but not limited to, various polygons, circles, ovals, irregular shapes, and the like) and, in turn, the groups of discrete binding detectors can be arranged into many different patterns (including, but not limited to, star patterns, zig-zag patterns, radial patterns, symbolic patterns, and the like).

In some embodiments, the order of specific discrete binding detectors 202 across the length 212 and width 214 of the measurement zone can be substantially random. In other embodiments, the order can be specific. For example, in some embodiments, a measurement zone can be ordered so that the specific discrete binding detectors 202 for analytes having a lower molecular weight are located farther away from the incoming gas flow relative to specific discrete binding detectors 202 for analytes having a higher molecular weight which are located closer to the incoming gas flow. As such, chromatographic effects which may serve to provide separation between chemical compounds of different molecular weight can be taken advantage of to provide for optimal binding of chemical compounds to corresponding discrete binding detectors.

In some embodiments, a measurement zone can be ordered so that the specific discrete binding detectors 202 for analytes having a lower polarity are located a farther distance from the incoming gas flow and specific discrete binding detectors 202 for analytes having a higher polarity are located closer to the incoming gas flow. Alternately, the discrete binding detectors 202 can be ordered in the opposite manner. In this way, an electric field can be applied near the measurement zones such that the gas samples flow through the electric field and effectively concentrate analytes from the gas samples in the area where the corresponding discrete binding detectors are located.

The number of discrete binding detectors 202 within a particular measurement zone can be from about 1 to about 100,000. In some embodiments, the number of discrete binding detectors 202 can be from about 1 to about 10,000. In some embodiments, the number of discrete binding detectors 202 can be from about 1 to about 1,000. In some embodiments, the number of discrete binding detectors can be from about 2 to about 500. In some embodiments, the number of discrete binding detectors can be from about 10 to about 500. In some embodiments, the number of discrete binding detectors can be from about 50 to about 500. In some embodiments, the number of discrete binding detectors can be from about 1 to about 250.

Each of the discrete binding detectors 202 can define at least a portion of one or more electrical circuits. By way of example, in some embodiments, each of the discrete binding detectors 202 can have one or more passive electrical circuits. The electrical properties of each electrical circuit can change upon binding, such as specific and/or non-specific binding, with a component from a gas sample.

The discrete binding detectors 202 can be functionalized with analyte binding receptors capable of specific binding and/or analyte binding receptors capable of non-specific binding. It will be appreciated that there are various chemistries which can be utilized to facilitate attachment of analyte binding receptors. By way of example, in the context of attachment to a graphene surface, covalent or non-covalent binding approaches can be used. Covalent binding approaches can include the formation of covalent bonds between free radicals or dienophiles of molecules to be attached or intermediates and C=C bonds of graphene layers. Covalent binding approaches can also include the formation of covalent bonds between organic functional groups of molecules to be attached or intermediates and oxygen groups of graphene oxide (a graphene derivative). As just one example, a diazonium salt can be heated producing a highly reactive free radical which attacks the $sp^2$ carbon atoms of graphene forming a covalent bond. The diazonium salt itself can be modified to contain the desired functional group(s) with which the graphene is functionalized or can include linking groups to which other desired functional group(s) can later be attached. Various approaches to the functionalization of graphene are described in Georgakilas et al., *Functionalization of Graphene: Covalent and Non-Covalent Approaches, Derivatives and Applications*, Chemical Reviews, 2012 Nov. 14;112(11):6156-214; U.S. Publ. Appl. No. 2011/0017587; and U.S. Publ. Appl. No. 2014/0275597, the content of all of which is herein incorporated by reference.

It will be appreciated that there are various structures that can be used as analyte binding receptors. Exemplary structures for binding can include, but are not limited to, antibodies, antibody fragments, nonimmuno-proteins, nucleic acids, other organic receptors, small molecule receptors, inorganic receptors, and the like.

Each particular discrete binding detector 202 can have one or more analyte binding receptors bound thereto. In some embodiments, all of the analyte binding receptors within a particular discrete binding detector can be the same with respect to their analyte binding properties. In other embodiments, at least some of the analyte binding receptors within a particular zone can be different from one another with respect to their analyte binding properties. In some embodiments, each discrete binding detector 202 can be unique. In some embodiments, discrete binding detectors 202 that are unique can be cross-reactive in that they bind to different portions or different configurations of the same chemical compound. In some embodiments, each discrete binding detector 202 can have a single passive sensor circuit. In other embodiments, each discrete binding detector can include multiple passive sensor circuits.

Figure 3:
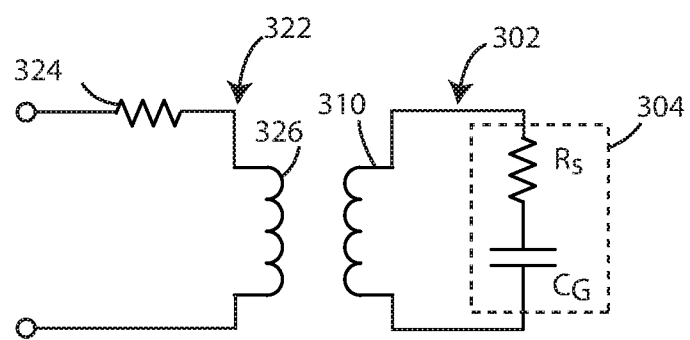
FIG. 3 is a circuit diagram of a passive sensor circuit and a portion of a reading circuit is shown in accordance with various embodiments herein.

FIG. 3 is a circuit diagram of a passive sensor circuit 302 and a portion of a reading circuit 322 is shown in accordance with various embodiments herein. The passive sensor circuit is generally a component of a disposable sensor test strip 140 (FIG. 1) and the reading circuit 322 is generally a component of the reading device 132 (FIG. 1). In some embodiments, the passive sensor circuit 302 can have a graphene varactor (variable capacitor) or metal-graphene-oxide capacitor 304 (wherein RS represents the series resistance and CG represents the varactor capacitor) coupled to an inductor 310. Graphene varactors can be prepared in various ways and with various geometries. As just one example, in some aspects, a gate electrode can be recessed into an insulator layer. A gate electrode can be formed by etching a depression into the insulator layer and then depositing an electrically conductive material in the depression to form the gate electrode. A dielectric layer can be formed on a surface of the insulator layer and the gate electrode. In some examples, the dielectric layer can be formed of a material, such as, aluminum oxide, hafnium dioxide, zirconium dioxide, hafnium silicate or zirconium silicate. A graphene layer can be disposed on the dielectric layer. In some aspects, the graphene layer can be a graphene monolayer. Contact electrodes can also be disposed on a surface of the graphene layer. Aspects of exemplary graphene varactors can be found in U.S. Publ. App. No. 2014/0145735, the content of which is herein incorporated by reference.

In various embodiments, the functionalized graphene layer (e.g., functionalized to include analyte binding receptors), which is part of the graphene varactor and thus part of a sensor circuit such as a passive sensor circuit, is exposed to the gas sample flowing over the surface of the measurement zone. The passive sensor circuit 302 can also have an inductor 310. In some embodiments, only a single varactor is include with each passive sensor circuit 302. In other embodiments, multiple varactors are included, such as in parallel, with each passive sensor circuit 302.

In the passive sensor circuit 302, the quantum capacitance of the electrical circuit changes upon binding between the analyte binding receptors and a component from a gas sample. The passive sensor circuit 302 can function as an LRC resonator circuit, wherein the resonant frequency of the passive sensor circuit 302 changes upon binding with a component from a gas sample.

The reading circuit 322 can be used to detect the electrical properties of the passive sensor circuit 302. By way of example, the reading circuit 322 can be used to detect the resonant frequency of the passive sensor circuit 302 and/or changes in the same. In some embodiments, the reading circuit 322 can include a reading coil having a resistance 324 and an inductance 326. The reading circuit 322 changes frequencies and takes impedance measurements to identify the resonant frequency of the passive sensor circuit 302. When the passive sensor circuit 302 is at its resonant frequency, a plot of the phase of the impedance of the reading circuit versus the frequency has a minimum (or phase dip frequency). Sensing can occur when the varactor capacitance varies in response to binding of analytes, which changes the resonant frequency, and the value of the phase dip frequency.

FIGS. 4-11 depict gas sampling devices having a variety of configurations. Those having skill in the art will appreciate that many of the individual elements disclosed in each of the configurations can be combined in a single gas sampling device, depending on the functionality of the gas sampling device desired.

As discussed above, a gas sampling device is generally configured to facilitate testing of a received gas sample. In multiple embodiments, the gas sampling device is configured to condition the gas sample to enhance the ability of the system to collect meaningful data from the sample. In such embodiments, the gas sampling device can incorporate a conditioning element that is configured to condition the gas sample.

Figure 4:
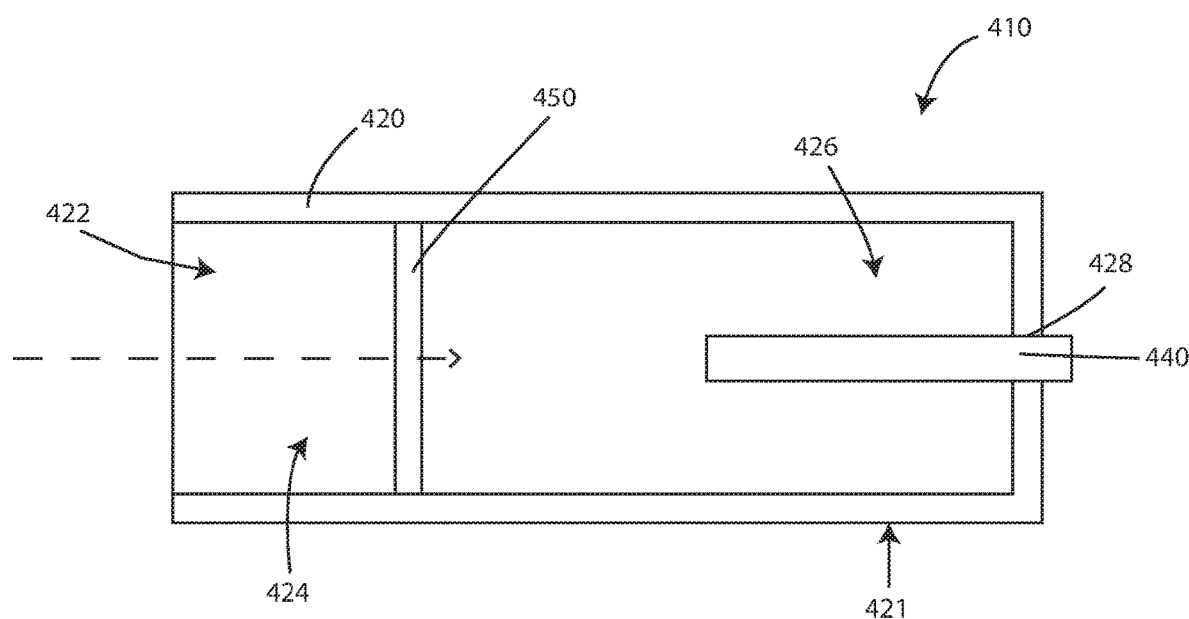
FIG. 4 is a schematic cross-sectional view of a gas sampling device in accordance with various embodiments.

FIG. 4 is a schematic cross-sectional view of a gas sampling device 410 incorporating one example conditioning element 450. Similar to the embodiment depicted in FIG. 1, the currently-described gas sampling device 410 has a housing 420 defining an airflow aperture 422, a gas testing chamber 426, a sensor receptacle 428, an airflow pathway 424, and a docking structure 421.

In embodiments consistent with the current figure, the conditioning element 450 is in communication with the airflow pathway 424 between the airflow aperture 422 and the gas testing chamber 426. In particular, the conditioning element 450 extends across the airflow pathway 424. However, it will be appreciated that in other embodiments the conditioning element 450 does not extend all the way across the airflow pathway. For example, in some embodiments, the conditioning element 450 can be disposed on or within a wall of a conduit or tube defining a portion of the airflow pathway. The conditioning element 450 is a filter element in some embodiments. The conditioning element 450 can include one or more materials that result in chemical modification of the gas sample, such as a VOC (volatile organic compound) filter, a desiccant, an oxidizing agent or a reducing agent. In some embodiments the conditioning element 450 is a heating element disposed across the airflow pathway. A heating element can be desirable for reducing the humidity of the gas sample and/or for increasing the reactivity of the gas sample with the intended sensor and/or for controlling temperature to adjust for variations in the ambient environment where the system is used.

While not specifically depicted, in some embodiments the gas sampling device 410 can have one or more components that are configured to recirculate the gas sample through the gas testing chamber 426, such as an airflow pump or fan and a recirculation airflow path, to maximize exposure of the gas sample to a gas sensor test strip. In some embodiments the gas sampling device 410 is configured to sealably contain the gas sample within at least the gas testing chamber such that the gas sample remains relatively stagnant and in contact with the sensor test strip 440. By way of example, the device can include valves both upstream and downstream of the gas testing chamber that can be selectively opened or closed to trap a gas sample within the gas testing chamber. In some embodiments, the device can include a diverting valve that can be selectively actuated, such as when the gas testing chamber traps a gas sample, in order to route additional gas that may come into the device (such as if a patient is still blowing into it) back out of the device through an exhaust pathway and/or port.

Figure 5:
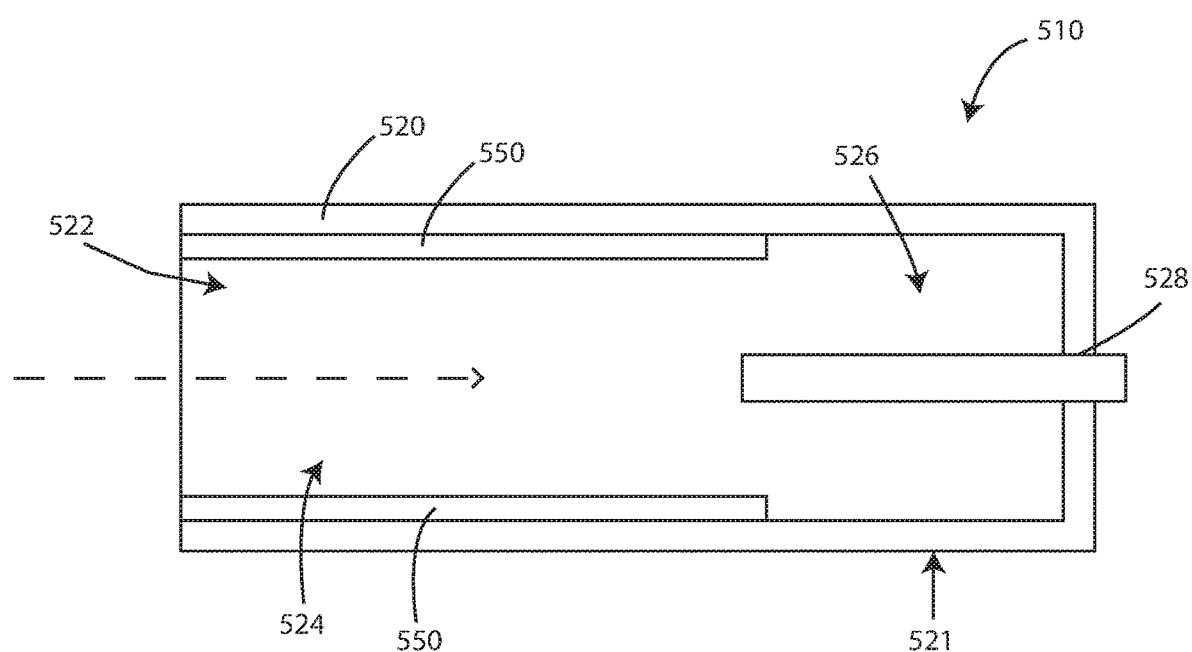
FIG. 5 is a schematic cross-sectional view of a gas sampling device in accordance with various embodiments.

FIG. 5 is a schematic cross-sectional view of a gas sampling device 510 having another example conditioning element 550 consistent with some embodiments. Similar to the embodiment depicted in FIG. 1, the currently-described gas sampling device 510 has a housing 520 defining an airflow aperture 522, a gas testing chamber 526, a sensor receptacle 528, an airflow pathway 524, and a docking structure 521.

In embodiments consistent with the current figure, the conditioning element 550 is in communication with the airflow pathway 524 between the airflow aperture 522 and the gas testing chamber 526. In particular, here the conditioning element 550 is disposed along at least a portion of the airflow pathway. In some embodiments the conditioning element 550 can extend into at least a portion of the gas testing chamber 526. The conditioning element 550 can be a variety of materials and components, including those mentioned above such as a material that results in the chemical modification of the gas sample, and a heating element In some examples a heating element can be positioned along, adjacent to, or within portions of the interior of the housing (including but not limited to the airflow pathway and/or gas testing chamber) that will contact the gas sample as it passes through the device. In some embodiments, the heating element (or elements) is configured to heat at least about 50, 60, 70, 80, 90, 95, 98, 99, or even 100% of the surfaces of the housing (such as interior surfaces) that contact the gas sample as it moves through the device, including but not limited to the airflow pathway and/or gas testing chamber.

Figure 6:
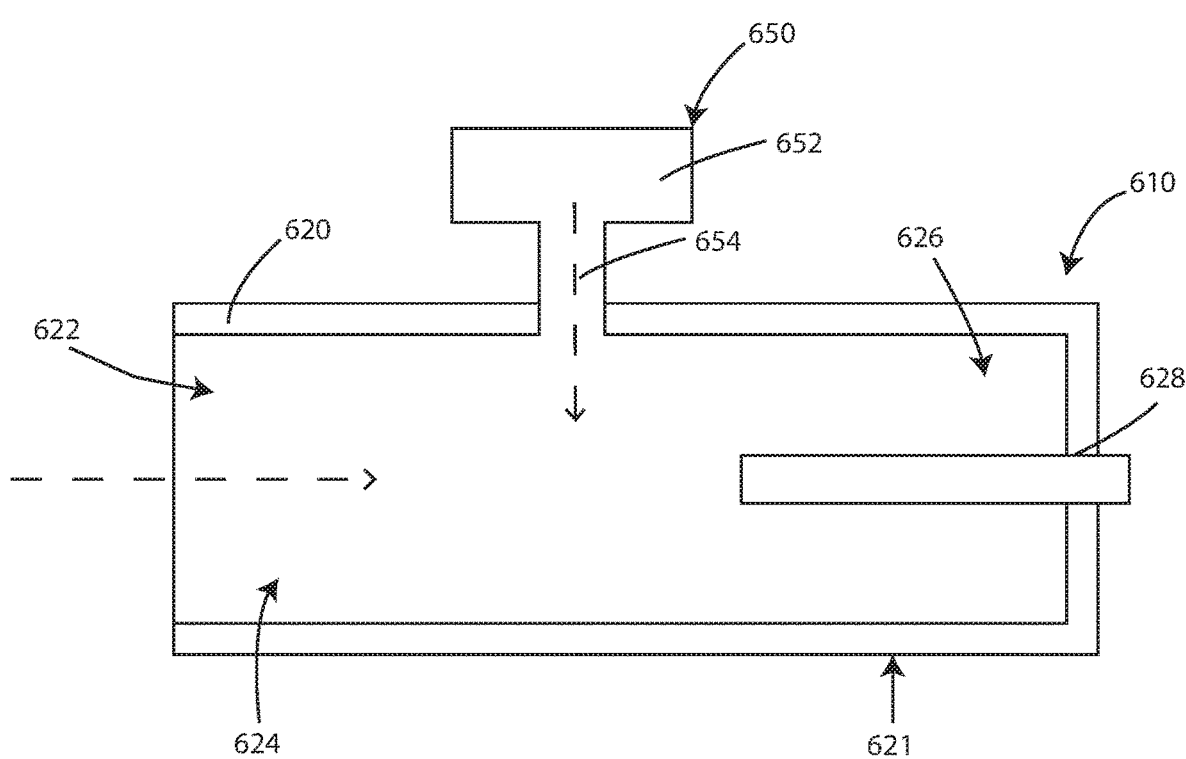
FIG. 6 is a schematic cross-sectional view of a gas sampling device in accordance with various embodiments.

FIG. 6 is a schematic cross-sectional view of a gas sampling device having another example conditioning element 650 consistent with some embodiments. Similar to the embodiment depicted in FIG. 1, the currently-described gas sampling device 610 has a housing 620 defining an airflow aperture 622, a gas testing chamber 626, a sensor receptacle 628, an airflow pathway 624, and a docking structure 621.

In embodiments consistent with the current figure, the conditioning element 650 is in communication with the airflow pathway 624 between the airflow aperture 622 and the gas testing chamber 626. In particular, here the conditioning element 650 can be a gas source in fluid communication with the gas testing chamber 626. The conditioning element 650 can define a gas reservoir 652 (in some embodiments) and a gas output 654 that is in fluid communication with the airflow pathway 624. In some embodiments the gas output 654 is in fluid communication with the gas testing chamber 626.

The gas source can be a variety of gases and combinations of gases that dilute the sample gas. Diluting the sample gas can be desirable to reduce the amount of moisture. In some embodiments the gas source is VOC-filtered air. In some other embodiments the gas source is nitrogen.

While FIGS. 4-6 each depict a gas sampling device having a single conditioning element, it should be appreciated that multiple combinations of conditioning elements can be incorporated in gas sampling devices consistent with the technology disclosed herein. It can be desirable to condition a gas sample in a multiple different ways to maximize sensor readability of the sample.

Figure 7:
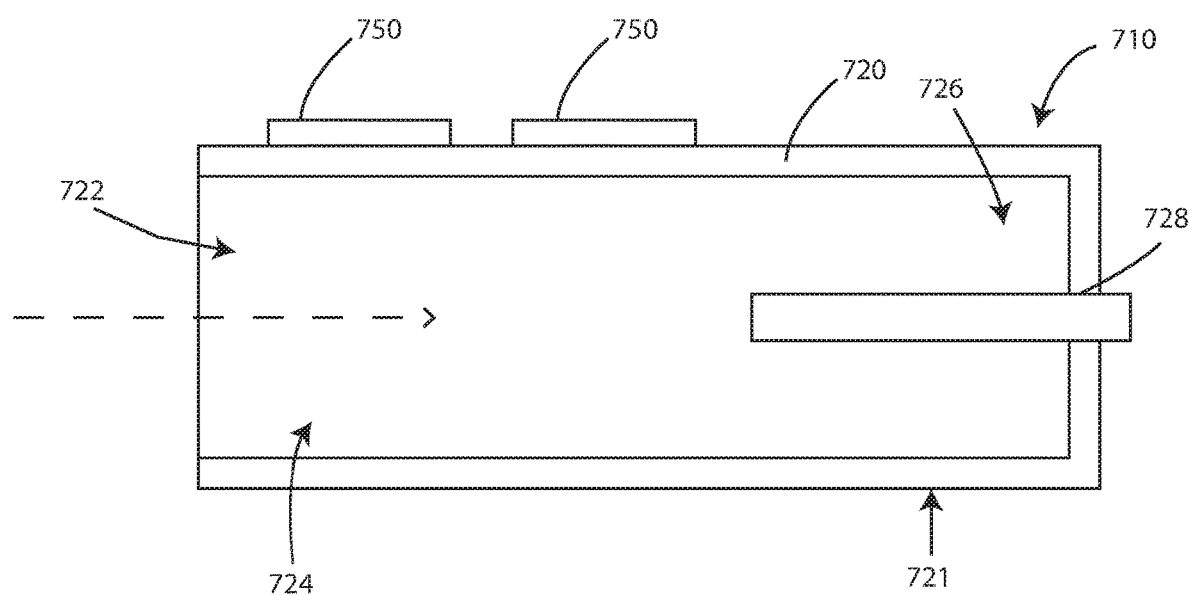
FIG. 7 is a schematic cross-sectional view of a gas sampling device in accordance with various embodiments.

FIG. 7 is a schematic cross-sectional view of another gas sampling device in accordance with various embodiments. Similar to the embodiment depicted in FIG. 1, the currently-described gas sampling device 710 has a housing 720 defining an airflow aperture 722, a gas testing chamber 726, a sensor receptacle 728, an airflow pathway 724, and a docking structure 721.

In embodiments consistent with the current figure, at least one sensor 750 is coupled to the housing. In particular, the sensor 750 is disposed on an exterior surface of the housing 720. The sensor 750 can be configured to sense a variety of types of data accessible at the exterior surface of the housing 720. In some embodiments, the sensor 750 can be a heart rate sensor that can, for example, collect data from a fingertip of a patient. In some embodiments, the sensor 750 can be a temperature sensor that can measure ambient temperature and/or the temperature of a patient's finger or lips. In some embodiments, the sensor 750 can measure ambient pressure.

Figure 8:
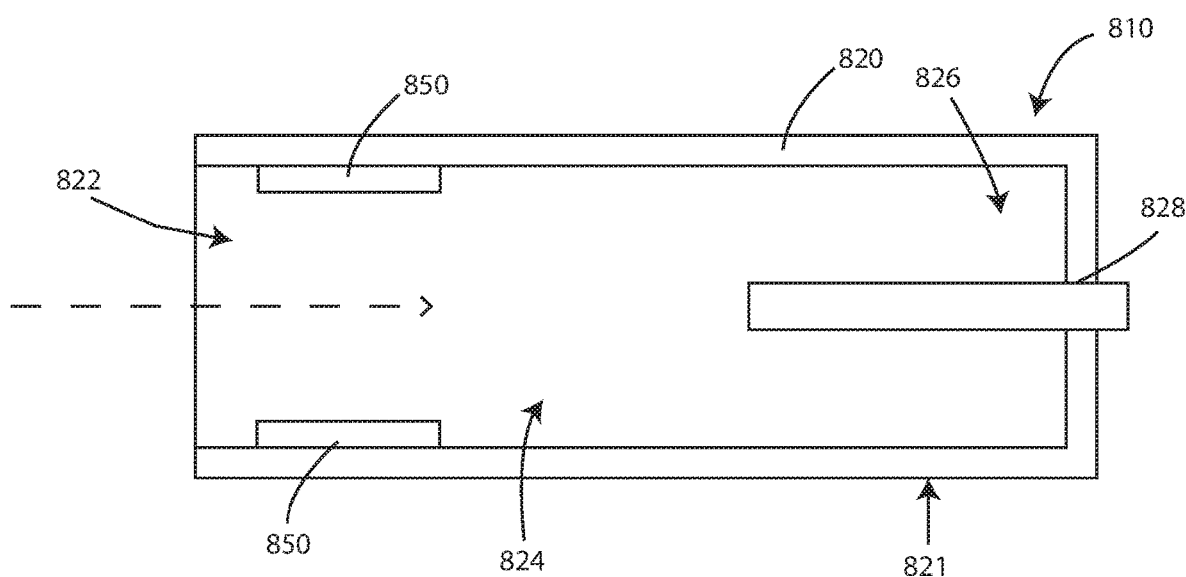
FIG. 8 is a schematic cross-sectional view of a gas sampling device in accordance with various embodiments.

FIG. 8 is a schematic cross-sectional view of another gas sampling device in accordance with various embodiments. Similar to the embodiment depicted in FIG. 1, the currently-described gas sampling device 810 has a housing 820 defining an airflow aperture 822, a gas testing chamber 826, a sensor receptacle 828, an airflow pathway 824, and a docking structure 821.

In embodiments consistent with the current figure, at least one sensor 850 is coupled to the housing. In particular, the sensor 850 is disposed in the airflow pathway 824. The sensor 850 can be configured to sense a variety of types of data accessible in the airflow pathway 824. In some embodiments, the sensor 850 can be a humidity sensor that can sense the humidity of the sample gas. In some embodiments, the sensor 850 can be a temperature sensor that can measure the temperature of the sample gas. In some embodiments, the sensor 850 can measure pressure and/or flow rate. In various embodiments, the sensor 850 can measure the carbon dioxide level in the sample gas, some embodiments of which will be described below with respect to FIG. 10.

Data collected from sensors depicted in FIGS. 7-8 can collect various types of data. In some embodiments, data such as heart rate, temperature, or other measurements can aid in diagnosing a patient in combination with tested gas data.

Figure 9:
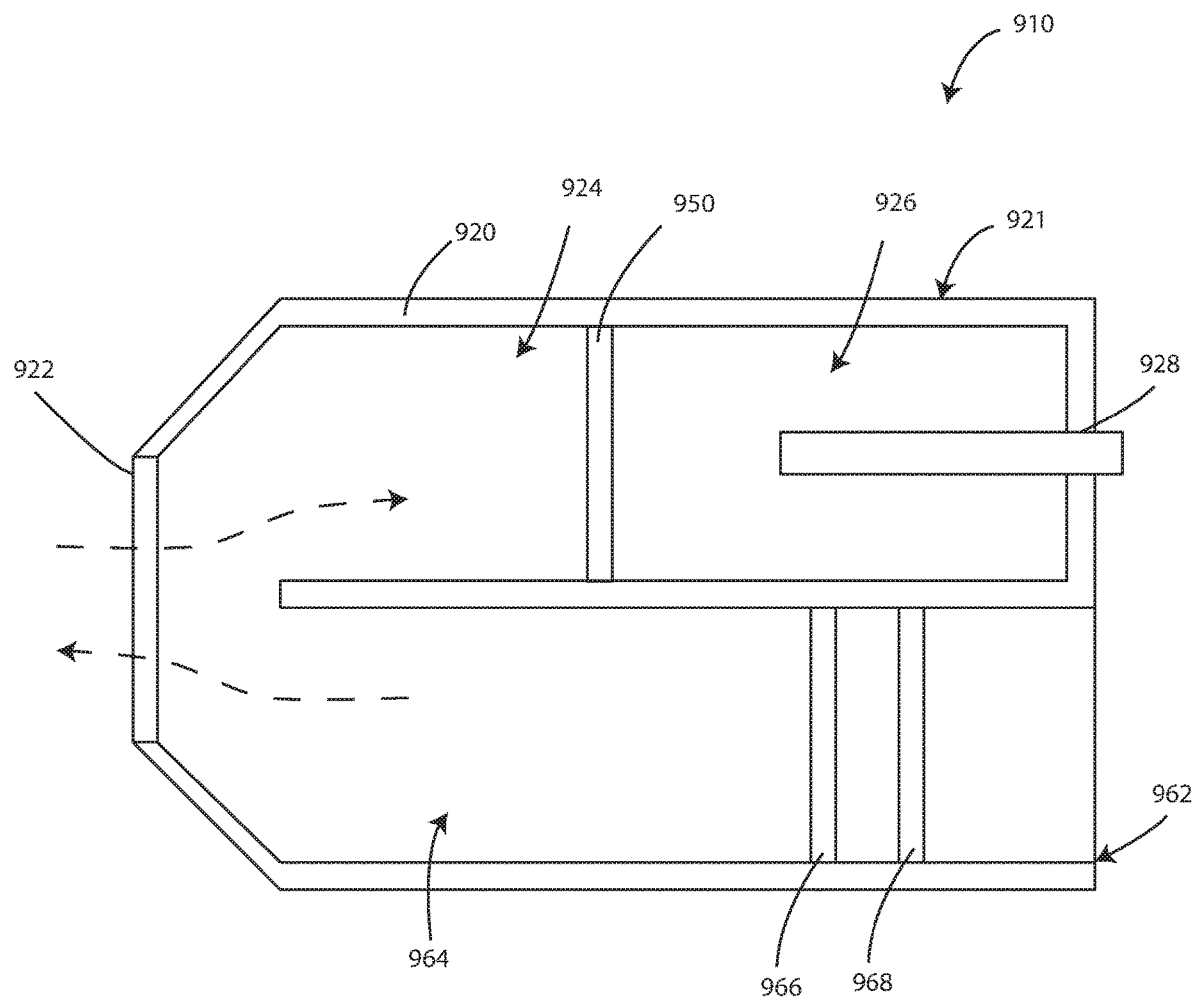
FIG. 9 is a perspective view of an example implementation of a gas sampling device in accordance with various embodiments.

FIG. 9 is a perspective view of an example implementation of a gas sampling device in accordance with various embodiments. Similar to the embodiment depicted in FIG. 1, the currently-described gas sampling device 910 has a housing 920 defining an airflow aperture 922, a gas testing chamber 926, a sensor receptacle 928, an airflow pathway 924, and a docking structure 921.

In embodiments consistent with the current figure, the housing 920 defines an inhalation pathway 964 and inhalation inlet 962 through which a patient inhales and the airflow pathway 924 through which the patient exhales, from which the gas sample is collected. In such embodiments the air that the patient inhales can be conditioned to improve the quality of the sample gas for sensing purposes. For example, a conditioning element 968 can be positioned in the inhalation pathway 964 to condition the inhaled air. The conditioning element 968 can be similar or the same as conditioning elements previously described, but in the current figure, the conditioning element 968 extends across the inhalation pathway. However, in some embodiments, the conditioning element 968 may not extend across the inhalation pathway or may only extend part way across the inhalation pathway. In some specific embodiments the conditioning element 968 is VOC filter.

In various embodiments a first one-way valve 950 can be disposed across the airflow pathway 924 between the airflow aperture 922 and the gas testing chamber 926. The first one-way valve can be configured to prevent airflow from the gas testing chamber 926 towards the airflow aperture 922. Similarly, in various embodiments a second one-way valve 966 can be disposed across the inhalation pathway 964 between the airflow aperture 922 and the inhalation inlet 962. The second one-way valve 966 can be configured to prevent airflow from the airflow aperture 922 towards the inhalation inlet 962. It is noted that some embodiments of gas sampling devices already described can incorporate a one-way valve even absent an inhalation pathway. Such a one-way valve can limit the exposure of the disposable sensor test strip to air other than the sample gas, such as ambient air.

Figure 10:
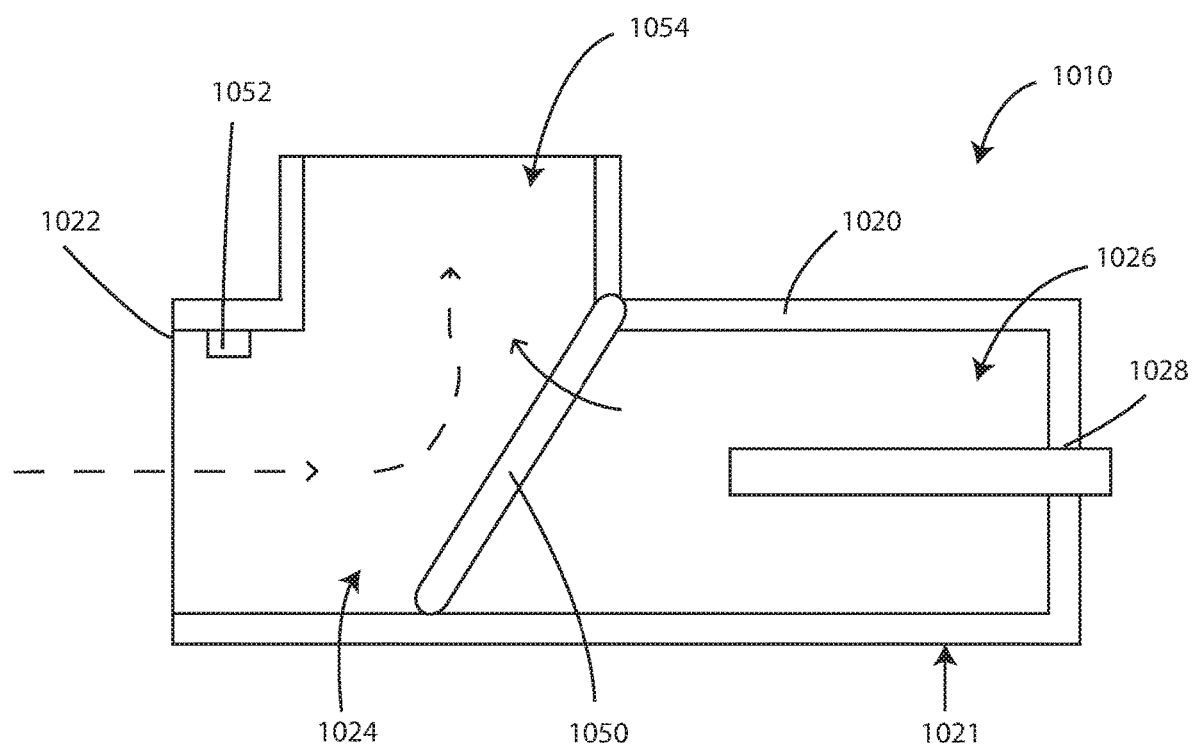
FIG. 10 is a schematic cross-sectional view of another gas sampling device in accordance with various embodiments.

FIG. 10 is a schematic cross-sectional view of another gas sampling device in accordance with various embodiments. Similar to the embodiment depicted in FIG. 1, the currently-described gas sampling device 1010 has a housing 1020 defining an airflow aperture 1022, a gas testing chamber 1026, a sensor receptacle 1028, an airflow pathway 1024, and a docking structure 1021. In embodiments consistent with the current figure the gas sampling device 1010 is configured to selectively (1) collect and (2) exhaust the exhaled gas.

The housing 1020 defines an exhaust port 1054 in fluid communication with the airflow pathway 1024. The gas sampling device 1010 has a diverter valve 1050 (or other component) that is configured to selectively route exhaled air to the exhaust port 1054 and the gas testing chamber 1026. The gas sampling device 1010 can have a sensor 1052 coupled to the housing 1020. The sensor 1052 is disposed in the airflow pathway 1024. The diverter valve 1050 can be in functional communication with the sensor 1052. The sensor 1052 can be configured to send one or more types of data that are measurable in the airflow pathway such as carbon dioxide, humidity, temperature, pressure, and flowrate.

In some embodiments the data collected by the sensor 1052 can dictate whether the exhaled air is exhausted from the housing 1020 or collected as sample gas in the gas testing chamber 1026. For example, the $CO_2$ content of the air from the patient can be monitored and the exhaled air can be diverted to the gas testing chamber 1026 when the CO₂ content plateaus. This can be desirable because it is believed that when the CO₂ content plateaus the exhaled air is most reflective of the gases and condition within the patient's body (and, therefore, most reflective of a possible disease state), rather than gases originating in the ambient air that were most recently inhaled and then rapidly exhaled before equilibrating with the interior environment with the lungs and/or alveoli therein.

Figure 11:
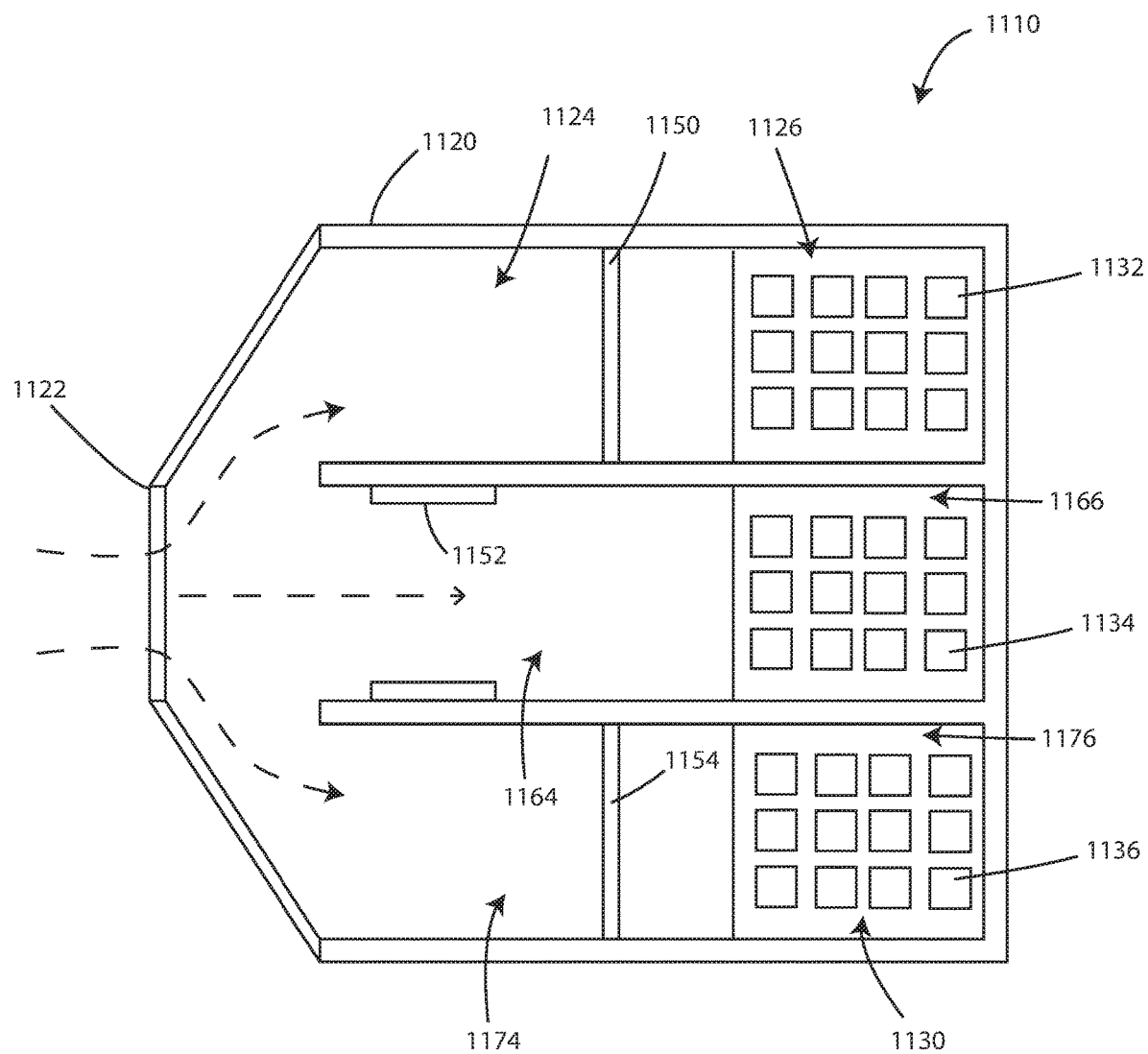
FIG. 11 is a schematic cross-sectional view of another gas sampling device in accordance with various embodiments.

FIG. 11 is a schematic cross-sectional view of another gas sampling device in accordance with various embodiments. Similar to the embodiment depicted in FIG. 1, the currently-described gas sampling device 1110 has a housing 1120, an airflow aperture 1122 and a docking structure (not visible). Unlike previous figures, the current figure is a facing view of measurement zones 1132, 1134, 1136 of an example disposable sensor test strip 1130. Furthermore, unlike embodiments previously described, the housing 1120 of the gas sampling device 1110 defines a plurality of airflow pathways 1124, 1164, 1174 each in fluid communication with a particular gas testing chamber 1126, 1166, 1176 (or discrete segments within a single gas testing chamber). In some cases, the plurality of airflow pathways 1124, 1164, 1174 may start from a single combined airflow pathway and may then be divided with an airflow manifold or similar structure.

A first airflow pathway 1124 is defined between the airflow aperture 1122 and a first gas testing chamber 1126 that is configured to receive a first measurement zone 1132 of the disposable sensor test strip 1130. A second airflow pathway 1164 is defined between the airflow aperture 1122 and a second gas testing chamber 1166 that is configured to receive a second measurement zone 1134 of the disposable sensor test strip 1130. A third airflow pathway 1174 is defined between the airflow aperture 1122 and a third gas testing chamber 1176 that is configured to receive a third measurement zone 1136 of the disposable sensor test strip 1130. While there are three airflow pathways and gas testing chambers depicted in the current embodiment, the housing 1120 can define fewer or additional airflow pathways and remain consistent with the technology disclosed herein. Furthermore, the gas sampling device 1110 can further incorporate an inhalation pathway described above with reference to FIG. 9.

The gas sampling device 1110 and/or each of the airflow pathways 1124, 1164, 1174 can incorporate conditioning elements, sensors, valves and combinations thereof, where such components can be consistent with those previously described herein. In embodiments consistent with the current figure, the first airflow pathway 1124 has a first conditioning element 1150, the second airflow pathway 1164 has a second conditioning element 1152, and the third airflow pathway 1174 has a valve 1154.

Figure 12:
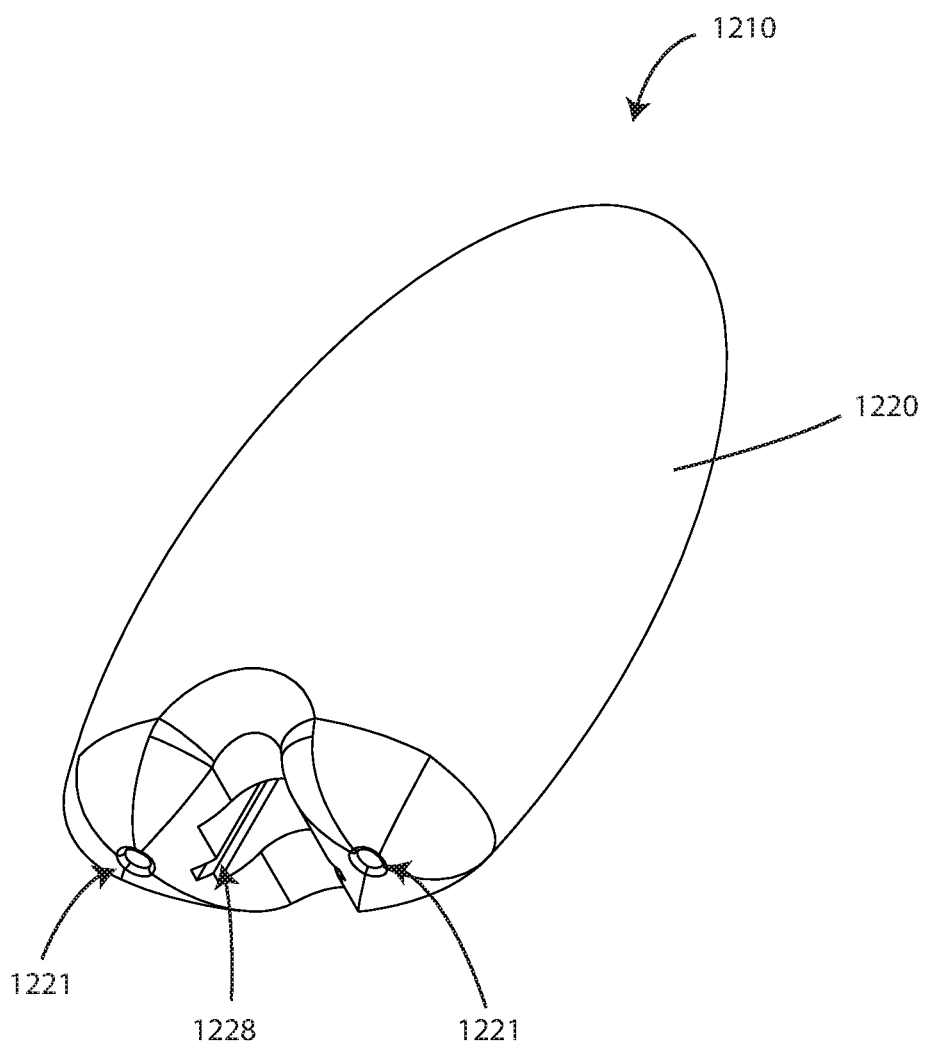
FIG. 12 is a perspective view of an example implementation of a gas sampling device in accordance with various embodiments.
Figure 13:
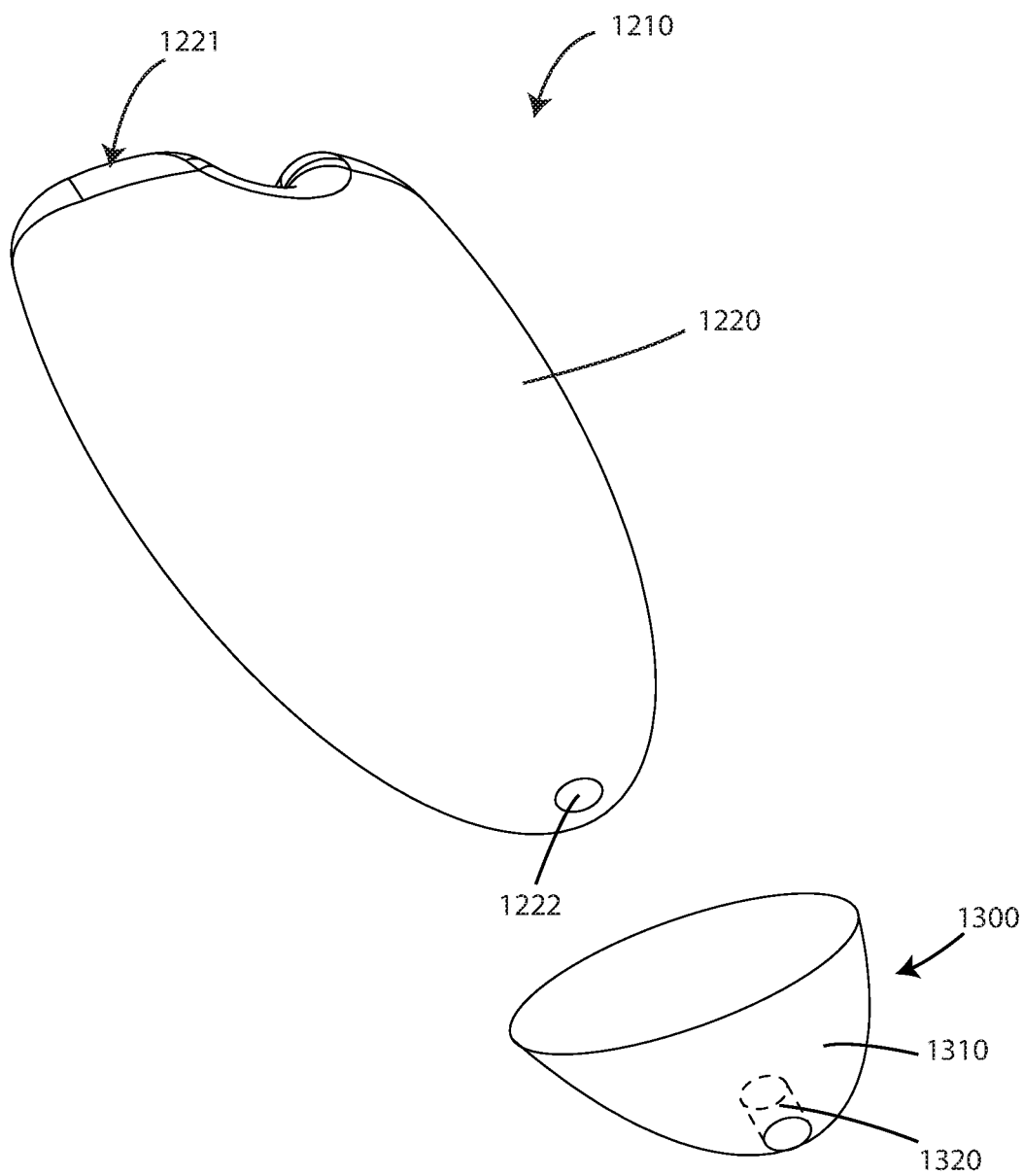
FIG. 13 is a perspective view of the device of FIG. 9 from a second perspective.

FIG. 12 is a perspective view of an example implementation of a gas sampling device 1210 in accordance with various embodiments, and FIG. 13 is a perspective view of the gas sampling device 1210 of FIG. 12 from a different perspective. The gas sampling device 1210 has a housing 1220 defining an airflow aperture 1222, a docking structure 1221, and a sensor receptacle 1228. Similar to embodiments depicted in the previous figures, the gas sampling device 1210 has an airflow pathway extending from the airflow aperture 1222 to a testing chamber, although the testing chamber and the airflow pathway are not visible in the perspective views. The gas sampling device 1210 can incorporate components such as valves, sensors, and conditioning elements described above.

FIG. 13 also depicts an example protective liner that was briefly mentioned above with respect to FIG. 1. The protective liner 1300 is a disposable mouthpiece configured to removably couple to the housing 1220 of the gas sampling device 1210 about the airflow aperture 1222. The protective liner 1300 is generally configured to prevent direct contact between a patient's mouth and the gas sampling device 1210. In embodiments, the disposable mouthpiece has an airflow pathway liner 1320 that is configured to be inserted through the airflow aperture 1222 to abut a portion of the airflow pathway (not visible) and the airflow aperture 1222.

Figure 14:
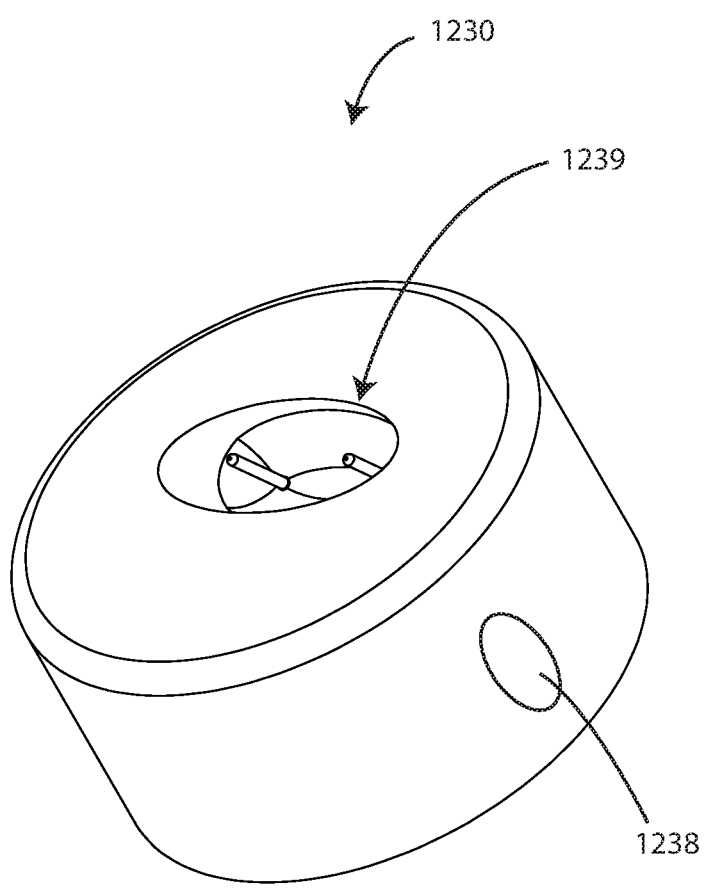
FIG. 14 is a perspective view of an example implementation of a base station in accordance with various embodiments.
Figure 15:
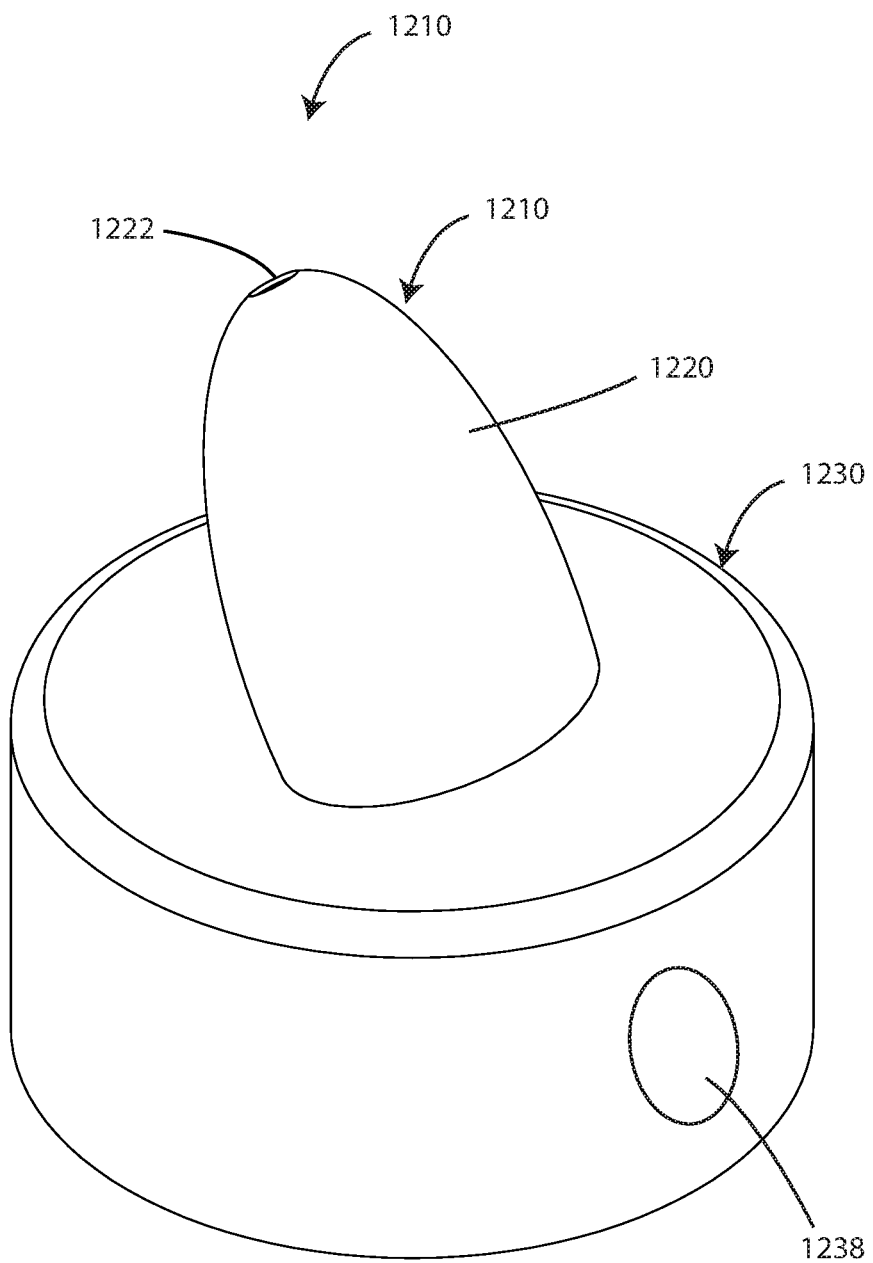
FIG. 15 is a perspective view of an example implementation of a system in accordance with various embodiments.

FIG. 14 is a perspective view of an example implementation of a docking station 1230 in accordance with various embodiments and FIG. 15 is a perspective view of an example implementation of a system in accordance with the embodiments depicted in FIGS. 12-14. The docking station 1230 has a mating structure 1239 that is configured to receive the docking structure 1221 of the gas sampling device 1210. The docking station 1230 also has a user interface 1238 that is configured to communicate data to a user, such as providing information on the status of the testing process and/or providing cues to the user regarding what steps to take next. In the current embodiment, and similar to embodiments already described, the docking station 1230 has internal components that are not visible in the current figures such as communication hardware, networking hardware, a processor, and memory.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which the present technology pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive.

We claim:

1. A gas sampling device comprising:
    a housing, the housing defining: an airflow aperture, a gas testing chamber,
    a sensor receptacle disposed along a long axis of the housing and within an airflow pathway within the gas testing chamber, the sensor receptacle configured to slidably receive a disposable sensor test strip within the gas testing chamber, the airflow pathway extending from the airflow aperture to the gas testing chamber,
    a docking structure configured to be physically received within a docking station;
    a heart rate sensor disposed on an exterior surface of the housing and configured to measure heart rate data from a fingertip of a patient: and
    the disposable sensor test strip comprising a plurality of discrete binding detectors disposed thereon.

2. The device of claim 1, further comprising a one-way valve disposed across the airflow pathway between the airflow aperture and the gas testing chamber.

3. The device of claim 1, further comprising a conditioning element in communication with the airflow pathway between the airflow aperture and the gas testing chamber.

4. The device of claim 3, wherein the conditioning element is a filter element disposed across the airflow pathway.

5. The device of claim 3, wherein the conditioning element is a gas source in fluid communication with the gas testing chamber.

6. The device of claim 3, wherein the conditioning element is a heating element disposed along a portion of the airflow pathway.

7. The device of claim 1, wherein the housing further defines an inhalation inlet and an inhalation pathway extending from the airflow aperture to the inhalation inlet, wherein a VOC-filter is disposed across the inhalation pathway.

8. The device of claim 7, further comprising a one-way valve disposed across the inhalation pathway between the inhalation inlet and the airflow aperture.

9. The device of claim 1, wherein the docking structure is configured to define an interference fit with the docking station.

\* \* \* \* \*